US012728169B2

(12) United States Patent
Paulson et al.

(10) Patent No.: US 12,728,169 B2
(45) Date of Patent: Sep. 8, 2026

(54) IMMUNE CELL RECEPTOR ANTIBODIES CONJUGATED TO HIGH AFFINITY SIGLEC-LIGANDS

(71) Applicant: The Scripps Research Institute, La Jolla, CA (US)

(72) Inventors: James C. Paulson, Del Mar, CA (US); Maidul Islam, San Diego, CA (US); Fabian Pfrengle, Klosterneuburg (AT); Matthew Macauley, Edmonton (CA); Shiteng Duan, San Diego, CA (US); Britni Arlian, Spring Valley, CA (US)

(73) Assignee: THE SCRIPPS RESEARCH INSTITUTE, La Jolla, CA (US)

(*) Notice: Subject to any disclaimer, the term of this patent is extended or adjusted under 35 U.S.C. 154(b) by 1106 days.

(21) Appl. No.: 17/755,382

(22) PCT Filed: Oct. 28, 2020

(86) PCT No.: PCT/US2020/057727

§ 371 (c)(1),
(2) Date: Apr. 27, 2022

(87) PCT Pub. No.: WO2021/086958

PCT Pub. Date: May 6, 2021

(65) Prior Publication Data

US 2023/0037822 A1 Feb. 9, 2023

Related U.S. Application Data

(60) Provisional application No. 62/926,753, filed on Oct. 28, 2019.

(51) Int. Cl.
*A61K 47/68* (2017.01)
*A61P 37/08* (2006.01)

(52) U.S. Cl.
CPC ...... *A61K 47/6849* (2017.08); *A61K 47/6807* (2017.08); *A61P 37/08* (2018.01)

(58) Field of Classification Search
CPC .................................................. A61K 47/6849
See application file for complete search history.

(56) References Cited

U.S. PATENT DOCUMENTS

| | | | |
|---|---|---|---|
| 3,561,444 | A | 2/1971 | Boucher |
| 3,703,173 | A | 11/1972 | Dixon |
| 4,051,842 | A | 10/1977 | Hazel et al. |
| 4,140,122 | A | 2/1979 | Kuhl et al. |
| 4,383,529 | A | 5/1983 | Webster |
| 4,624,251 | A | 11/1986 | Miller |
| 4,635,627 | A | 1/1987 | Gam et al. |
| 2019/0151444 | A1 | 5/2019 | Paulson et al. |

FOREIGN PATENT DOCUMENTS

| | | | |
|---|---|---|---|
| WO | WO-2007056525 | A2 | 5/2007 |
| WO | WO-2021086958 | A1 | 5/2021 |

OTHER PUBLICATIONS

"International Application Serial No. PCT/US2020/057727, International Search Report mailed Feb. 10, 2021", 4 pgs.
"International Application Serial No. PCT/US2020/057727, Written Opinion mailed Feb. 10, 2021", 8 pgs.
Akkapeddi, Padma, et al., "Construction of homogeneous antibody-drug conjugates using site-selective protein chemistry", Chem. Sci., 2016, 7(5), 2954-63, (Feb. 12, 2016), 2954-2964.
Bednar, Kyle J., et al., "Exploiting CD22 to Selectively Tolerize Autoantibody Producing B-cells in Rheumatoid Arthritis", ACS Chem Biol. Apr. 19, 2019; 14(4): 644-654. doi:10.1021/acschembio.8b01018., (Apr. 19, 2019), 644-654.
Bednar, Kyle J., et al., "Human CD22 Inhibits Murine B-cell Receptor Activation in a Human CD22 Transgenic Mouse Model", J Immunol. Nov. 1, 2017; 199(9): 3116-3128. doi: 10.4049/jimmunol.1700898., (Nov. 1, 2017), 3116-3128.
Blixt, O., et al., "Sialoside Specificity of the Siglec Family Assessed Using Novel Multivalent Probes", The Journal of Biological Chemistry, 278(33), (2003), 31007-31019.
Blixt, Ola, et al., "Printed covalent glycan array for ligand profiling of diverse glycan binding proteins", Proc Natl Acad Sci USA, 101(49), (Dec. 7, 2004), 17033-17038.
Blixt, Ola, et al., "Sialoside Analogue Arrays for Rapid Identification of High Affinity Siglec Ligands", J. Am. Chem. Soc., 130(21), (2008), 6680-6681.
Duan, Shiteng, et al., "CD33 recruitment inhibits IgE-mediated anaphylaxis and desensitizes mast cells to allergen", J Clin Invest. 2019;129(3):1387-1401, (Mar. 2019), 1387-1401.
Elliott, Steve, "Structural Requirements for Additional N-Linked Carbohydrate on Recombinant Human Erythropoietin", The Journal of Biological Chemistry, vol. 279, No. 16, Issue of Apr. 16, pp. 16854-16862, 2004, (Feb. 2, 2004), 16854-16862.
Galli, Stephen J., et al., "Recruiting CD33 on mast cells to inhibit IgE-mediated mast cell-dependent anaphylaxis", J Clin Invest. 2019; 129(3):955-957. https://doi.org/10.1172/JCI127100., (Mar. 2019), 955-957.
Kawasaki, Norihito, et al., "CD22 Regulates Adaptive and Innate Immune Responses of B Cells", J Innate Immun 2011;3:411-419. DOI: 10.1159/000322375., (Dec. 17, 2010), 411-419.
Macauley, Matthew S., et al., "Antigenic liposomes displaying CD22 ligands induce antigen-specific B cell apoptosis", Journal of Clinical Investigations, 123(7), (2013), 3074-3083.
Orgel, Kelly A., et al., "Exploiting CD22 on Antigen-Specific B-Cells to Prevent Allergy to the Major Peanut Allergen Ara h 2", J Allergy Clin Immunol. Jan. 2017; 139(1): 366-369.e2. doi:10.1016/j.jaci.2016.06.053., (Jan. 2017), 366-369.
Pang, Lijuan, et al., "Encapsulating An Immunosuppressant Enhances Tolerance Induction by Siglec Engaging Tolerogenic Liposomes", Chembiochem. Jul. 4, 2017; 18(13): 1226-1233. doi: 10.1002/cbic.201600702., (Jul. 4, 2017), 1226-1233.

(Continued)

*Primary Examiner* — Prema M Mertz
(74) *Attorney, Agent, or Firm* — SCHWEGMAN LUNDBERG & WOESSNER, P.A.

(57) ABSTRACT

Described herein are Siglec ligand-antibody conjugates and compositions thereof that are useful for suppressing unwanted immune responses such as allergies and anaphylaxis.

3 Claims, 13 Drawing Sheets

(56) References Cited

OTHER PUBLICATIONS

Pfrengle, Fabian, et al., "Copresentation of Antigen and Ligands of Siglec-G Induces B Cell Tolerance Independent of CD22", Journal of Immunology, 191(4), (Aug. 2013), 1724-1731.
Rillahan, Cory D., "Click and Pick: Identification of Sialoside Analogues for Siglec-Based Cell Targeting", Angew. Chem. Int. Ed., 51, (2012), 11014-11018.
Sochaj, Alicja M., et al., "Current methods for the synthesis of homogeneous antibody-drug conjugates", Biotechnology Advances 33 (2015) 775-784, (May 14, 2015), 775-784.
Tang, Feng, et al., "Chemoenzymatic synthesis of glycoengineered IgG antibodies and glycosite-specific antibody-drug conjugates", Nat Protoc. Aug. 2017; 12(8): 1702-1721. doi:10.1038/nprot.2017.058, (Aug. 2017), 1702-1721.
"International Application Serial No. PCT US2020 057727, International Preliminary Report on Patentability mailed May 12, 2022", 10 pgs.

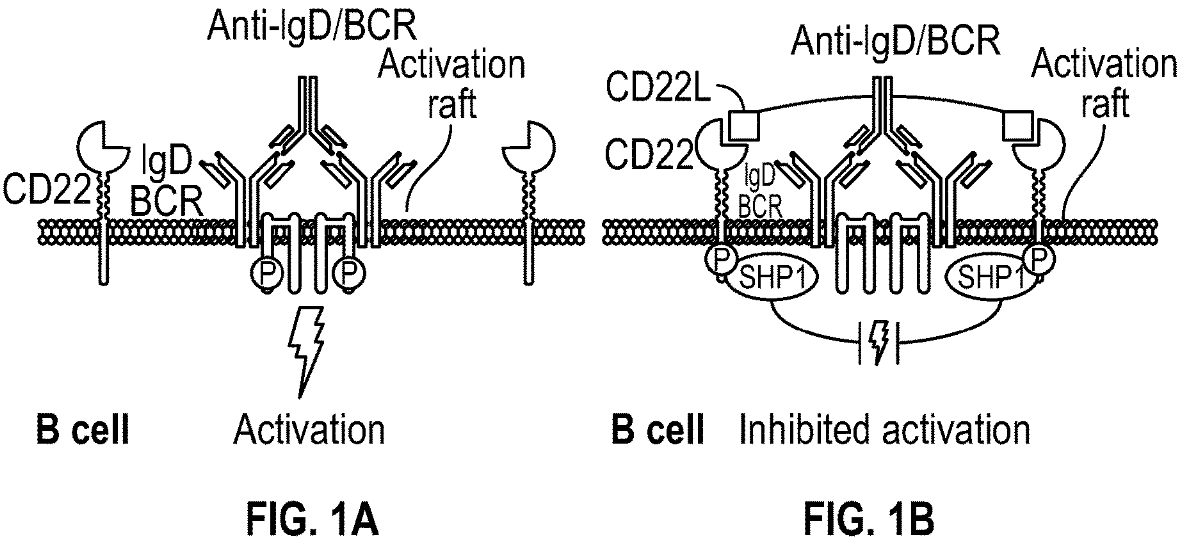
FIG. 1A
FIG. 1B
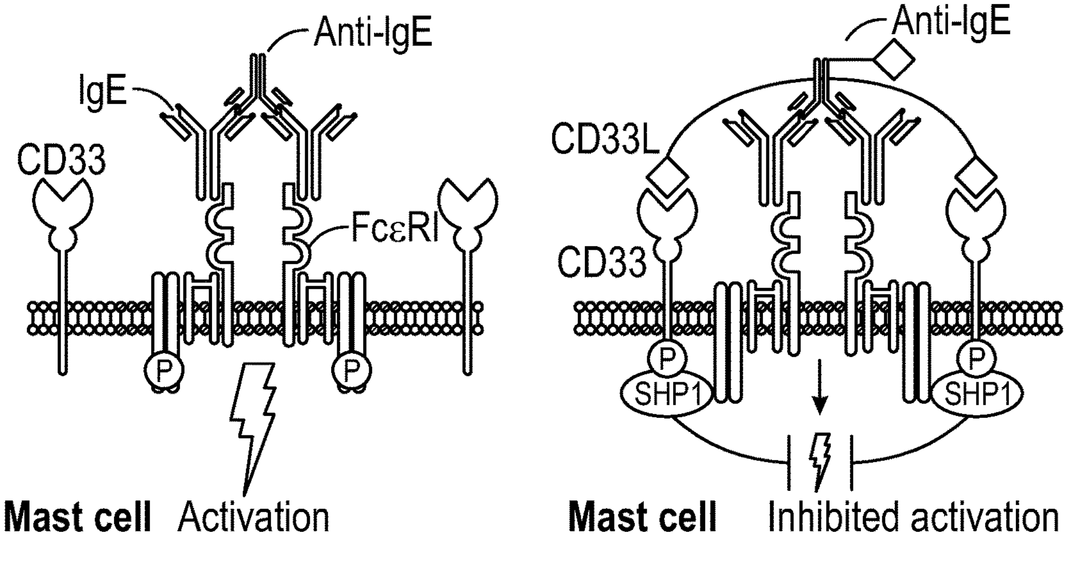
FIG. 1C
FIG. 1D

CD33L mCD22L

CD22L

Step I

Step II

IMMUNE CELL RECEPTOR ANTIBODIES CONJUGATED TO HIGH AFFINITY SIGLEC-LIGANDS

CROSS-REFERENCE TO RELATED APPLICATION

This application is a U.S. national stage filing under 35 U.S.C. § 371 from International Application No. PCT/US2020/057727, filed on 28 Oct. 2020, and published as WO2021/086958 on 6 May 2021, which claims the priority of U.S. provisional application Ser. No. 62/926,753, filed Oct. 28, 2019, and which applications and publication are hereby incorporated herein by reference in their entirety.

FEDERAL FUNDING

This invention was made with government support under R01AI099141, R01AI050143, AR01AI132790, U19AI136443, and P01HL107151 awarded by the National Institutes of Health. The government has certain rights in the invention.

BACKGROUND

Unwanted immune responses are a major cause of medical conditions that affect millions of peoples' daily lives ranging from allergies, asthma, autoimmune diseases, Grave's disease, thrombotic thrombocytopenic purpura and idiopathic thrombocytopenic purpura, and development of inhibitory antibodies to biotherapeutic medicines. Methods to suppress immune responses that cause these conditions offer the potential to prevent unwanted suffering and save lives.

For example, a primary feature of autoimmune diseases is the loss of B-cell tolerance and the inappropriate production of autoantibodies. More than 80 distinct autoimmune diseases have been described, including multiple sclerosis, rheumatoid arthritis, and systemic lupus erythematosus. A commonly used biological that is used to treat certain B-cell autoimmune conditions is rituximab (Rituxan/Mabthera). Although rituximab can be effective, side effects are common including anemia, infections, nausea, diarrhea, and Hepatitis B reactivation.

For allergies and asthma, while the global prevalence continues to increase, treatment is far from ideal. Clinical responses to current therapies, such as inhaled corticosteroids and leukotriene modifiers, are heterogeneous and even with optimal treatment there is a substantial burden of unaddressed disease.

Upon exposure of allergen, mast cells primed with anti-allergen-immunoglobulin E (IgE) release granules and powerful chemical mediators, such as histamine, cytokines, granulocyte macrophage colony-stimulating factor (GM-CSF), leukotrienes, heparin, and many proteases into the environment. These chemical mediators directly cause the characteristic acute symptoms of allergies. Eosinophils are recruited to the sites of chemical mediator release, which exacerbates the longer-term symptoms of diseases such as asthma.

Conventional allergen-specific immunotherapy involves inducing tolerance to antigen, which is time consuming and risky. For example, antigens administered to induce tolerance can induce anaphylaxis instead. Drugs such as omalizumab (Xolair) block circulating IgE from binding to FcεRI on mast cells, but its clinical efficacy remain questionable, and omalizumab has been demonstrated to be non-efficacious in a significant percentage of patients. Omalizumab does not actively crosslink IgE and does not neutralize antigen-specific IgE antibodies.

Therefore, a need exists for agents that can control activation of various immune-related cell types.

SUMMARY

Compositions and methods are described herein that are useful for suppressing unwanted immune cell responses. The compositions and methods involve use of antibodies conjugated to ligands for inhibitory sialic acid binding immunoglobulin lectins (Siglecs). Such inhibitory Siglecs are present on various immune cell types and can suppress immune cell activation, but the inhibitory Siglecs are not necessarily positioned near the cellular receptors responsible for activating an immune response. By conjugating Siglec ligands to antibodies that recognize and bind to endogenous cellular receptors on immune cells, the activation of such immune cells is more efficiently suppressed. Hence, the antibodies employed are 'anti-receptor' antibodies.

Anti-receptor antibodies conjugated to Siglec ligands suppress cellular activation by recruiting the inhibitory Siglec to the receptor. Examples of activating receptors that can be bound by the anti-receptor antibodies include the B cell receptors (BCRs), receptors for the Fc region of immunoglobulin E (FcεR1), toll like receptors (TLRs), T-cell receptors (TCRs), receptors for a Fc region of immunoglobulin E (FcεRI), or complexes thereof. Examples of Siglecs that can suppress activation of activating receptors are CD22 (Siglec-2), CD33 (Siglec-3), Siglec-5, Siglec-6, Siglec-7, Siglec-8, Siglec-9, and Siglec-10.

For example, a major activating-receptor on mast cells is FcεRI, which forms a complex with anti-allergen IgE (IgE/FcεRI complex). Anti-IgE antibodies can bind to endogenous IgE that is bound to the FcεRI receptor and ligate the IgE/FcεRI receptor complex causing activation of the mast cells and release of granule contents that cause allergy symptoms, and in severe cases, anaphylaxis. However, use of anti-IgE antibodies conjugated to CD33 Siglec ligands (anti-IgE-CD33L conjugates) as described herein can desensitize mast cells. Such desensitization occurs when the anti-IgE antibodies bind to the IgE/FcεRI receptor complex and the conjugated CD33 Siglec ligand interacts with the CD33 Siglec to suppress and prevent mast cell activation. Binding by the anti-IgE-CD33L conjugates can therefore prevent and treat anaphylaxis and allergies.

In another example, activating B cell receptors (BCRs) include membrane bound IgD or IgM. Endogenous anti-IgD or anti-IgM can cause activation of B cells by ligating the corresponding IgD or IgM BCR. However, use of anti-IgD or anti-IgM antibody that is conjugated to a CD22 Siglec ligand can suppress activation by recruiting the inhibitory CD22 Siglec to the B cell receptor complex. Hence, such anti-IgD-Siglec ligand or anti-IgM-Siglec ligand conjugates can be used for B cell depletion as an alternative to an agent like rituximab.

However, conjugation of just one Siglec ligand to an anti-receptor antibody is generally not sufficient for optimal immune suppression. Instead, more than one, more than two, or more than five, or more than ten, or more than eleven, or more than twelve, or more than thirteen, or more than fourteen, or more than fifteen of the same Siglec ligands are generally conjugated to one antibody.

Therefore, described herein are conjugates between at least two Siglec ligands and an anti-receptor antibody, where the Siglec ligands and the anti-receptor antibody are covalently linked. In general, each Siglec ligand is conjugated to the anti-receptor antibody at a site that is not in the antigen binding site of the anti-receptor antibody. The Siglec ligands can, for example, be ligands for Siglec-2 (CD22), Siglec-3 (CD33), or Siglec-8.

Methods are also described herein that involve administration of a composition that includes one or more of the Siglec ligand-antibody conjugates to a subject. The subject can be suffering from, or be suspected of suffering from, an immune disease or immune condition. Examples of immune diseases or immune conditions that can be treated include, for example, allergies, allergic rhinitis, allergic asthma, non-allergic asthma, atopic dermatitis, allergic gastroenteropathy, anaphylaxis, urticaria, food allergies, allergic bronchopulmonary aspergillosis, parasitic diseases, interstitial cystitis, hyper-IgE syndrome, ataxia-telangiectasia, Wiskott-Aldrich syndrome, athymic lymphoplasia, IgE myeloma, graft-versus-host reaction, allergic purpura, rheumatoid arthritis, ulcerative colitis, crones disease, immune thrombocytopenia (ITP), thrombotic thrombocytopenic purpura (TTP).

DESCRIPTION OF THE FIGURES

FIG. 1A-I D schematically illustrate the impact of Siglec ligand-antibody conjugates on immune cell activity receptors. FIG. 1A illustrates activation of B cells induced by an anti-IgD B cell receptor (IgD BCR) antibody. FIG. 1B schematically illustrates suppression of B cell activation when anti-IgD is conjugated to CD22L as a result of CD22 being recruited to the IgD BCR. FIG. 1C schematically illustrates mast cell activation when anti-IgE antibodies ligate to the mast cell IgE/FcεRI complex. FIG. 1D schematically illustrates that when anti-IgE is conjugated to CD33L, activation and degranulation of the mast cell is suppressed as a result of the inhibitory CD33 being recruited to the IgE/FcεR1 receptor complex.

FIG. 2A shows a schematic illustrating an antibody conjugated to synthetic high affinity Siglec ligand (SiglecL) (top) and structures of exemplary high affinity ligands (bottom) for human CD33 (CD33L) murine CD22 (mCD22L) and human CD22 (CD22L). FIG. 2B shows a reaction scheme for generating an example of a Siglec ligand-antibody conjugate, where n is 2 to 10. In step 1, functional group 1 (FG1) is an azide, alkyne, aldehyde, ketone, thiol, maleimide, hydrazine, hydroxy-amine, alkene, iodo-benzene, or aryl boronic acid. In step 2, various functional groups can be used for FG1 and FG2. For example, FG1 can be azide while FG2 can be alkyne; or FG1 can be aldehyde while FG2 can be hydrazine; or FG1 can be thiol while FG2 can be maleimide; or FG1 can be alkene while FG2 can be Iodobenzene or aryl boronic acid; or FG1 can be ketone while FG2 can be alkoxy-amine.

FIG. 3A illustrates methods for chemical conjugation of Siglec ligands to antibodies. FIG. 3B illustrates characterization of the anti-IgD-mCD22L antibody conjugated Siglec ligand on an SDS gel. FIG. 3C illustrates characterization of the anti-IgE-CD33L antibody conjugated Siglec ligand on an SDS gel. The TCEP (Tris 2-carboxyethyl phosphine hydrochloride) reduces the disulfide bonds of the antibody to generate heavy (MW 50-60 KDa) and light (22-25 KDa) chains (see arrows) where the changes of molecular weight clearly show addition of the linker (PEG6-N3) and Siglec ligand (Alkyne-mCD22L or Alkyne-CD33L).

FIG. 4A shows that mCD22L-anti-IgD conjugates (lowest trace) suppress calcium flux by splenocytes in WT BALB/cByJ mice. FIG. 4B shows that mCD22L-anti-IgD in CD22KO Hy10 C57BL/6J mice does not inhibit calcium flux. The CD22 receptor is knocked out in the CD22KO Hy10 C57BL/6J mice.

FIG. 5A graphically illustrates the concentration dependence for binding of the unconjugated anti-IgE, the N3-anti-IgE and the CD33L-anti-IgE to human IgE in an ELISA assay. The results show that the effective concentration required to achieve half maximal binding of the N3-anti-IgE and CD33L-anti-IgE are within 2-fold of that required for binding of the unconjugated anti-IgE. FIG. 5B graphically illustrates that IL-6 cytokine production is suppressed by CD33L-anti-IgE compared to IL-6 production induced by unconjugated anti-IgE or N3-anti-IgE antibodies in bone marrow derived mast cells (BMMC) from $hFc\varepsilon RI^+/CD33^+$ transgenic mice pre-sensitized with human IgE. Results in FIG. 5B are representative of 3 independent experiments and the data were analyzed by One-way ANOVA followed by Tukey's multiple comparison test (*P<0.001 and P<0.0001). FIG. 5**C graphically illustrates the amounts of interleukin 6 (IL-6) released upon activation of bone marrow derived mast cells (BMMCs) by various anti-IgE antibodies obtained from different sources. Bone marrow derived mast cells (BMMCs) from $hFc\varepsilon R1^+/CD33^+$ mice were pre-sensitized with anti-OVA-human IgE (1 μg/100 k cells) overnight at 37° C. The pre-sensitized BMMCs were then treated with various clones of anti-IgE (10 μg/100 k cells), and IL-6 cytokine production was measured. The results are representative of two independent experiments.

FIG. 6A graphically illustrate suppression of passive cutaneous anaphylaxis by CD33L-anti-IgE conjugates in $hFc\varepsilon RI^+$ $CD33^+$ mice that express human CD33 mice (hFcεR1+mFcεR1−MCPT5Cre+$hCD33^{+/+}$; referred to as human CD33 expressing transgenic mice) (n=4). FIG. 6B graphically illustrates that both anti-IgE and CD33L-anti-IgE trigger passive cutaneous anaphylaxis in $hFc\varepsilon RI^+$ $CD33^{-/-}$ mice that did not express the human CD33 Siglec (hFcεR1+mFcεR1-MCPT5Cre-$hCD33^{-/-}$ mice) (n=4). The results in FIGS. 6A-6B were analyzed by One-way ANOVA followed by Tukey's multiple comparison test (*P<0.001 and **P<0.0001).

FIG. 7A graphically illustrates that compared to unconjugated anti-IgE or N3-anti-IgE antibodies, the CD33L-anti-IgE conjugates suppress passive systematic anaphylaxis in NSG-SGM3-CD34+ humanized mice (n=2). The results in FIG. 7A were analyzed by Two-way ANOVA followed by Tukey's test (*P<0.05,P<0.01,*P<0.001 **P<0.0001). FIG. 7B also graphically illustrates that CD33L-anti-IgE conjugates suppress passive systematic anaphylaxis in NSG-SGM3-CD34+ humanized mice (n=2). FIG. 7C graphically illustrates that CD33L-anti-IgE conjugates protect mice from passive systematic anaphylaxis at five hours after challenge with anti-IgE (n=2), but that control mice treated with PBS are not protected from systematic anaphylaxis. Results in FIG. 7B-7C were analyzed by Two-way ANOVA followed by Sidak's multiple test (*P=0.0002 and ****P<0.0001). AT reflects the changes in rectal temperature. The symbol ‡ indicates that the mice were found dead.

FIG. 8A graphically illustrates the impact of the CD33L conjugated to anti-IgE on induction of passive systemic anaphylaxis in human CD34+ stem cell 'humanized mice' (NSG-SGM3 mice that are populated with human mast cells). FIGS. 8B and 8C also graphically illustrates that CD33L-anti-IgE conjugates suppress passive systematic anaphylaxis in NSG-SGM3-CD34+ humanized mice at time=0 and time=5 h, respectively. Mice were pre-sensitized with one clone of anti-ovalbumin (OVA)-human IgE (11B6) and 2 different clones of anti-peanut antigen IgE (anti-Arah2-hIgE, 2C9 and 16A8). (400 ng/mouse). One day later mice were treated twice (at time=0 hour and time=5 h hour) with anti-human IgE with/without CD33L (2.5 μg/mice) and assessed for anaphylaxis by drop in temperature, revealing little or no anaphylaxis at that time. FIG. 8D graphically illustrates the effects of antigen challenge of the mice evaluated as shown in FIGS. 8B-8C. After another 24 hours, the mice treated as illustrated in FIGS. 8B-8C were administered OVA-liposomes (OVA-LP; 0.2 ml of 1 mM lipid, 0.05% OVA-lipid in phosphate buffered saline) intravenously. FIG. 8E graphically illustrates the effects of antigen challenge of the mice evaluated for FIGS. 8B-8C. After another 24 hours the mice treated as illustrated in FIGS. 8B-8C were administered peanut extract (10 μg in 0.2 ml phosphate buffered saline) intraperitoneally. After challenge with ovalbumin or peanut antigen, the change in rectal temperature of mice was measured at 10-minute intervals. The results show that treatment of anti-IgE-CD33L protects mice from anaphylaxis, and that the mice are subsequently desensitized to subsequence challenge. Results in FIGS. 8A-8E were analyzed by Two-way ANOVA followed by Bonferroni Test (*P=0.0332,P=0.0021,*P<0.0002 ****P<0.0001).

DETAILED DESCRIPTION

Figure 2A:
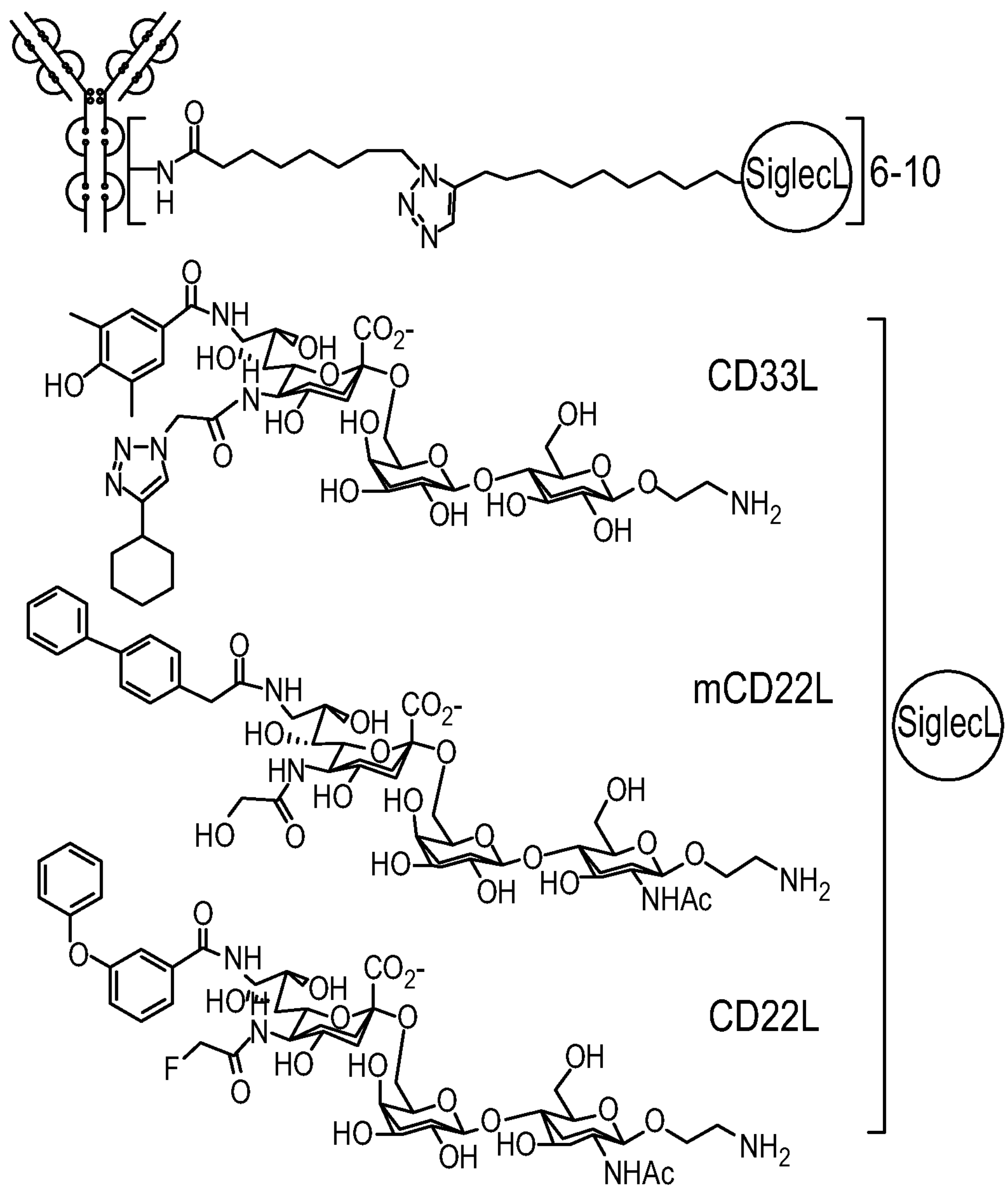
FIG. 2A-2B illustrate conjugation of Siglec ligands to antibodies.

Conjugates, compositions and methods are described herein that are useful for suppressing immune reactions. The conjugates include a ligand for an inhibitory sialic acid-binding Ig-like lectin (Siglec ligand) conjugated or linked to an antibody that binds to an immune cell activating receptor or receptor complex (an anti-receptor antibody). The anti-receptor antibody recognizes and binds to an immune cell receptor/receptor complex resulting in recruitment of the corresponding Siglec by the Siglec ligand, and suppression of immune cell activation.

Antibodies

The anti-receptor antibodies bind to immune cell receptors or to immune cell complexes that can activate the immune cell. Such immune cell receptors include B cell receptors (BCRs), receptors for the Fc region of immunoglobulin E (FcεRI), toll like receptors (TLRs), T-cell receptors (TCRs), cytokine receptors, or complexes thereof. For example, the anti-receptor antibodies can bind directly to B cell receptors, directly to FcεRI, directly to toll like receptors (TLRs), directly to cytokine receptors, or directly to T-cell receptors (TCRs).

However, the anti-receptor antibodies can also bind indirectly to IgD or IgM B cell receptors, indirectly to FcεRI, indirectly to toll like receptors (TLRs), indirectly to cytokine receptors, or indirectly to T-cell receptors (TCRs), by binding to a component of a B cell receptor complex, a component of a FcεR1 complex, a component of a TLR, a component of a cytokine receptor, or a component of a TCR.

Examples of components that can complex with B cell receptors include antigens that bind to the IgD or IgM receptors on the B cell membrane. Examples of components that can complex with FcεRI include IgE antibodies. Hence, the anti-receptor antibodies can, for example, be anti-IgE antibodies.

The anti-receptor antibodies employed are conjugated to Siglec ligands at sites within the anti-receptor antibodies that do not interfere with antigen binding. For example, conjugation of the anti-receptor antibodies to Siglec ligands should not inhibit the ability of the anti-receptor antibodies to form the types of intramolecular and intermolecular associations and bonds that the antibodies would form when non-conjugated. In particular, for example, the site of conjugation to Siglec ligands within the antibodies is not the antigen-binding site of the antibodies. In some cases, antibodies employed are conjugated to Siglec ligands at sites within the antibodies that do not interfere with antibody self-assembly.

For example, the anti-receptor antibodies can be linked to the Siglec ligand via a portion of the anti-receptor antibody constant region that is not involved in maintaining the secondary, tertiary, or quaternary structure of the antibody, and not involved in antigen binding.

The anti-receptor antibodies can be any functionally intact antibodies or functionally intact fragments thereof. The anti-receptor antibodies can be IgA, IgD, IgG, IgE, or IgM antibodies. In some cases, the Siglec ligands are conjugated to IgG anti-receptor antibodies.

In some cases, the anti-receptor antibodies are directed to receptors on a B cell receptors (BCR) that include a membrane bound IgD or IgM that is non-covalently associated with other proteins to form an IgD BCR or IgM BCR.

In some cases, the anti-receptor anti-10 BCR antibodies bind the IgD BCR portion of the IgD that is not involved in the association of IgD with other BCR proteins.

In some cases, the anti-receptor antibodies bind to IgE or to the FcεRI portions of the IgE/FIERI complex. The anti-receptor anti-IgE or the anti-receptor anti-FcεRI antibodies bind to portions of these proteins that are not involved in forming the IgE/FcεRI complex.

In some cases, the anti-receptor antibodies are directed to IgE antibodies. For example, such anti-receptor antibodies anti-IgE antibodies can bind endogenous IgE antibodies at a portion of the constant region that is not involved in forming the IgE structure or performing the function of the IgE antibody. Such a binding site of the anti-IgE antibody can be in any of the Cε1, Cε2, Cε3, and Cε1 domains of the IgE antibody that is not involved in IgE self-assembly, antigen binding, receptor binding, or other IgE functions.

In some cases, the anti-receptor antibodies can bind to a TCR-α, TCR-β chain, CD3, TCR ζ-chain accessory molecule, or an antigen bound to the TCR. In some cases, the Toll-like receptor is a TLR1, TLR2, TLR3, TLR4, TLR5, TLR6, TLR7, TLR8, TLR9, TLR10, TLR11, TLR12, and TLR13. The anti-receptor antibodies can bind to any such TLRs, or an antigen bound to any such TLRs.

Siglecs

There are fourteen human Siglecs, most of which are expressed by one or more cell types of the human immune system. Siglecs can regulate signaling of immune cells mediated by functional domains on the outside of the cell and the inside of the cell. The extra cellular portion of the Siglecs contains an N-terminal immunoglobulin (Ig) domain that binds to sialic acid bearing ligands and that influences the organization of the Siglec on the surface of the cell. The cytoplasmic domains of Siglecs contain regulatory motifs that can regulate cell signaling receptors. Siglecs can have one or more Immunoreceptor Tyrosine Inhibitory Motif (ITIM) or ITIM-like motifs called inhibitory Siglecs, which can mediate suppression of the activation of activitory receptors on immune cells. Such inhibitory Siglecs can have the following structural ITIM domain: (Ile/Val/Leu/Ser)-X-Tyr-X-X-(Leu/Val), where X is any amino acid.

Examples of inhibitory Siglec receptors found on mast cells include Siglec-2 (CD22), Siglec-3 (CD33), Siglec-5, Siglec-6, Siglec-7 and Siglec-8. Examples of inhibitory receptors on B cells include CD22 and Siglec-10. Other inhibitory receptors such as Siglec-9 are found on neutrophils. However, the conjugates are generally designed to target CD33 (Siglec-3) receptors on mast cells or CD22 (Siglec-2) receptors on B cells.

Siglec Ligands

The antibody conjugated Siglec ligands described herein can target and mediate the desensitization of immune responses to antigens. Although some antibodies may contain sialic acids, such antibodies cannot function in the same manner as the antibody-Siglec ligands described herein, for example because they cannot bind properly to the Siglec. The sialic acids that can sometimes be naturally present on antibodies do not have sufficient avidity and specificity for Siglec ligands to inhibit or desensitize immune responses.

The Siglec ligands described herein can, for example, bind to cell inhibitory Siglecs such as Siglec-2 (CD22), Siglec-3 (CD33), and/or Siglec-8.

Siglec-2 (also known as CD22) is expressed on B cells and functions as a negative regulator of B-cell receptor signaling. Normally, upon antigen binding to the B-cell receptor, the tyrosine residues in the immuno-receptor tyrosine-based inhibitory motifs (ITIMs) of CD22 are quickly phosphorylated and recruit protein tyrosine phosphatase SHP-1, which dephosphorylates the B-cell receptor and dampens the B cell response (Nitschke & Tsubata, 2004; Tedder et al., 2005). Thus, CD22 is important for setting the threshold of B-cell receptor signaling. CD22 is also known to regulate the activity of toll like receptors (TLRs) on B cells.

Siglec-3 (also known as CD33) is expressed on myeloid precursors in the bone marrow mostly in the more mature stages of the granulocytic lineage. For example, CD33 (Siglec-3) is typically found on mast cells and basophils.

Siglec-8 is a protein that in humans is encoded by the SIGLEC8 gene. Siglec-8 is expressed by human eosinophils, mast cells, and basophils-immune effector cell types that are involved in asthma, allergy, and anaphylaxis.

Siglec-3 and Siglec-8 are useful targets for treatment of allergic diseases and other immune-related conditions. For example, degranulation of mast cells causes bronchio-constriction, anaphylaxis, and recruitment of eosinophils, which is a hallmark of active asthma. In some cases, Siglec-2 is also a useful target for treatment of immune-related conditions.

The most common sialic acids naturally found in humans are N-acetylneuraminic acid (Neu5Ac) and 9-O-acetyl-N-acetylneuraminic acid (9-O-Ac-Neu5Ac). In most other animals (with the notable exception of chickens) Neu5Ac co-exists with N-glycolylneuraminic acid (Neu5Gc), which has a hydroxyl group at the terminus of the N-acyl group. Structures of N-acetylneuraminic acid (Neu5Ac) and N-glycolylneuraminic acid (Neu5Gc) are shown below.

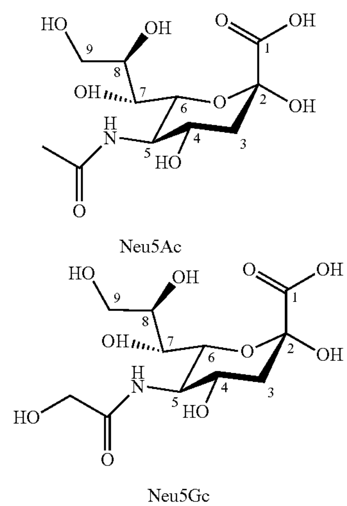

Neu5Ac

Neu5Gc

Siglec ligands employed in the conjugates, compositions and methods described herein are not natural Siglec ligands. For example, the Siglec ligands can have one or more substitutions (replacements) of the substituents that are present in natural sialic acids. Hence, the Siglec ligands employed herein can have various substituents at one or more of positions 1-9 of a sialic acid. For example, in some cases the Siglec ligands can be a compound of Formula I.

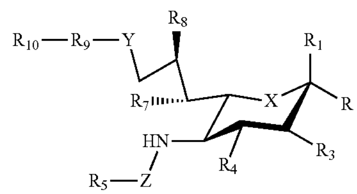

where:

X can be a methylene ($CH_2$) or a heteroatom (e.g., O, N, or S);

R can be a linker, an antibody, or $R_2$-$R_6$;

$R_1$ can be hydrogen, carboxylate, aldehyde (CHO), phosphate or sulfate;

$R_2$ can be a bond, a heteroatom, an alkene, an alkyne, an alkoxy, an alkyl, an alkyl-heterocycloalkyl-alkyl, a hydroxy, a heterocycle, or an oligosaccharide;

$R_3$, $R_4$, $R_7$ and $R_8$ can each independently be hydrogen, azido, amino, or hydroxyl;

$R_5$ can be a hydrogen, alkyl, alkene, alkyne, aryl, alkylaryl, heteroaryl, or alkylheteroaryl, wherein the alkyl, alkene, aryl, alkylaryl, heteroaryl, or alkylheteroaryl group(s) can be substituted with one or more substituents selected from hydroxy, amino, azido, cyano, nitro, halo, alkyl, $CF_3$, alkoxy, carboxylate, ether, cycloalkyl, lower alkenyl, lower alkynyl, phenyl, benzyl, phenoxy, heteroaryl, alkylheteroaryl, heteroarylalkyl, amidoheteroaryl, alkoxyamidoheteroaryl, or alkylhalide group;

$R_6$ can be an antibody;

Y can be a heteroatom, amino, carbamate, carboxyl, carboxylate, methylene, amide, —$CH_2$-carbamate, —$CH_2$-sulfonamide, —$CH_2$-amide, sulfonyl, —$CH_2$-sulfonyl, sulfonamide, urea, $CH_2$-urea, thiourea, or —$CH_2$-thiourea;

Z can be a carbonyl, carboxylate, methylene, acyl, aryl, heteroaryl, sulfonyl, —$CH_2$-sulfonyl, sulfonamide, —$CH_2$-sulfonamide, urea, —$CH_2$-urea, thiourea, —$CH_2$-thiourea;

$R_9$ can be a hydrogen, hydroxyl, alkyl, alkoxy, aryl, arylalkyl, arylalkoxy, alkoxyaryl, heteroaryl, alkylheteroaryl, or heterocycle, where the $R_9$ alkyl, alkoxy, alkylamino, aryl, arylalkyl, arylalkoxy, alkoxyaryl, heteroaryl, alkylheteroaryl, or heterocycle group(s) can be substituted with one or more substituents selected from hydrogen, hydroxy, alkyl, alkyne, alkoxy, amino, azido, cyano, nitro, halo, haloalkyl, $CF_3$, carboxylate, ether, or cycloalkyl groups; and, $R_{10}$ can be a hydrogen, alkyl, aryl, oxyaryl, heteroaryl, cycloalkyl, or bicycloalkyl, where the $R_{10}$ alkyl, aryl, oxyaryl, heteroaryl, cycloalkyl, or bicycloalkyl group(s) can be substituted with one or more substituents selected from hydrogen, alkyl, halo, $CF_3$, alkoxy, amino, azido, cyano, or nitro.

Various Siglec ligands may not have one or more of the groups listed for the $R_1$-$R_{10}$ substituents. However, at least one of the R, $R_5$, $R_9$ and $R_{10}$ groups has a substituent that is not found in natural Siglec ligands. In some cases, the Siglec ligands used in the compositions and methods described herein have at least one unnatural R, $R_5$ or $R_9$ substituent.

For example, some of the Siglec ligands can have Formula II:

II

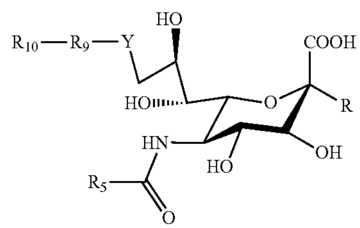

where the R, $R_5$, $R_9$ and $R_{10}$ groups are as defined herein.

In some cases the $R_5$ alkyl, alkene, aryl, alkylaryl, heteroaryl, or alkylheteroaryl can have 1 to 2, or 1 to 3, or 1 to 4 substituents selected from one or more substituents selected from hydroxy, amino, azido, cyano, nitro, halo, alkyl, $CF_3$, alkoxy, carboxylate, ether, cycloalkyl, lower alkenyl, lower alkynyl, phenyl, benzyl, phenoxy, heteroaryl, alkylheteroaryl, heteroarylalkyl, amidoheteroaryl, alkoxyamidoheteroaryl, or alkylhalide groups. In some cases, the R5 alkyl, alkene, aryl, alkylaryl, heteroaryl, or alkylheteroaryl groups can have 1, 2, 3, 4, or 5 substituents selected from halo, alkyl, $CF_3$, alkoxy, carboxylate, ether, cycloalkyl, lower alkenyl, lower alkynyl, phenyl, benzyl, phenoxy, heteroaryl, alkylheteroaryl, heteroarylalkyl, amidoheteroaryl, alkoxyamidoheteroaryl, or alkylhalide groups.

In some cases, the R9 alkyl, alkoxy, aryl, arylalkyl, arylalkoxy, alkoxyaryl, heteroaryl, alkylheteroaryl, or heterocycle group(s) can have 1 to 2, or 1 to 3, or 1 to 4 substituents selected from hydrogen, hydroxy, alkyl, alkyne, alkoxy, amino, azido, cyano, nitro, halo, haloalkyl, $CF_3$, carboxylate, ether, or cycloalkyl groups. In some cases, the R9 alkyl, alkoxy, aryl, arylalkyl, arylalkoxy, alkoxyaryl, heteroaryl, alkylheteroaryl, or heterocycle group(s) can have 1, 2, 3, 4, or 5 substituents selected from hydrogen, hydroxy, alkyl, alkyne, alkoxy, amino, azido, cyano, nitro, halo, haloalkyl, $CF_3$, carboxylate, ether, or cycloalkyl groups.

In some cases, $R_{10}$ alkyl, aryl, oxyaryl, heteroaryl, cycloalkyl, and/or bicycloalkyl group(s) can have 1 to 2, or 1 to 3, or 1 to 4 substituents selected from hydrogen, alkyl, halo, $CF_3$, alkoxy, amino, azido, cyano, or nitro groups. In some cases, $R_{10}$ alkyl, aryl, oxyaryl, heteroaryl, cycloalkyl, and/or bicycloalkyl group(s) can have 1, 2, 3, 4, or 5 substituents selected from hydrogen, alkyl, halo, $CF_3$, alkoxy, amino, azido, cyano, or nitro groups.

Examples of Siglec ligands that can be used in the conjugates include those listed in Table 1.

TABLE 1

| Examples of Siglec Ligands |
|---|
| 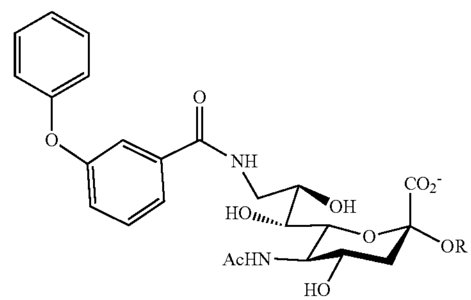 |
| 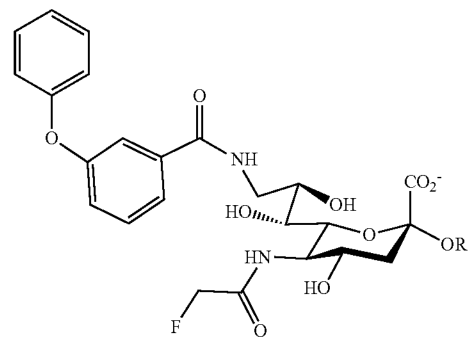 |
| 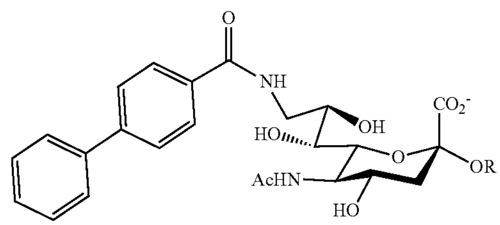 |
| 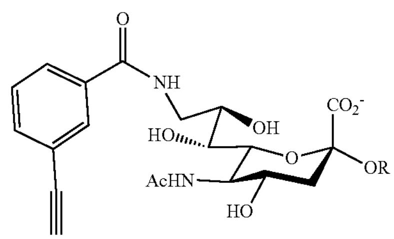 |

TABLE 1-continued
| Examples of Siglec Ligands |
| --- |
| 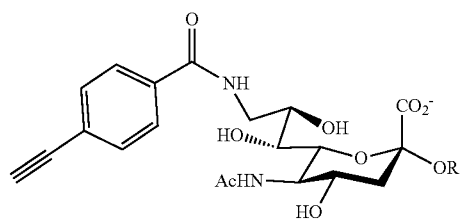 |
| 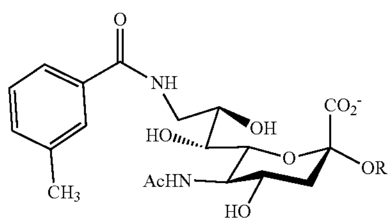 |
| 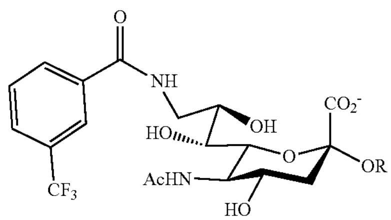 |
| 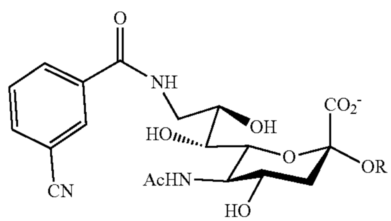 |
| 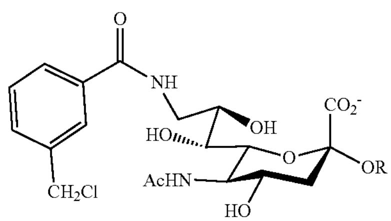 |
| 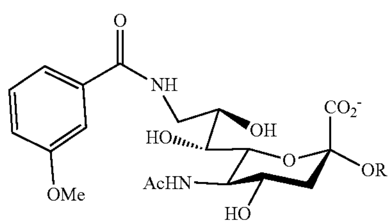 |
TABLE 1-continued
| Examples of Siglec Ligands |
| --- |
| 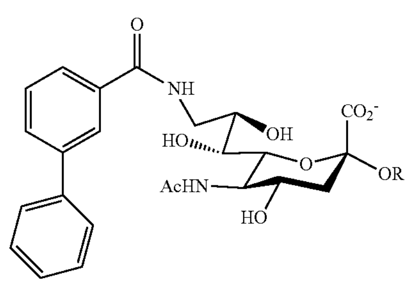 |
| 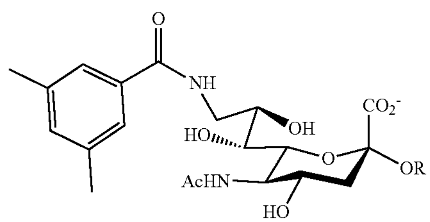 |
| 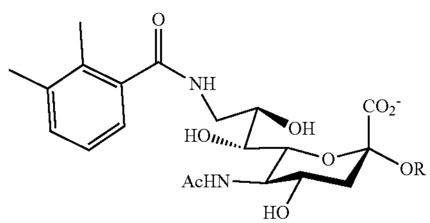 |
| 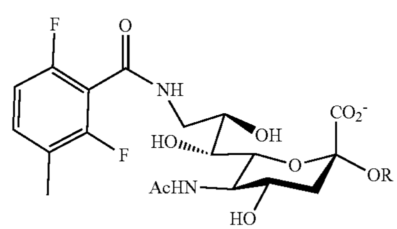 |
| 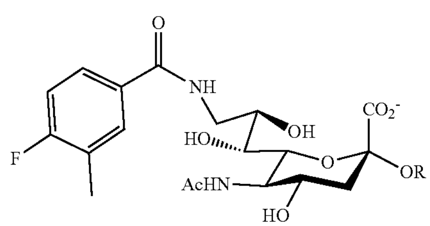 |
| 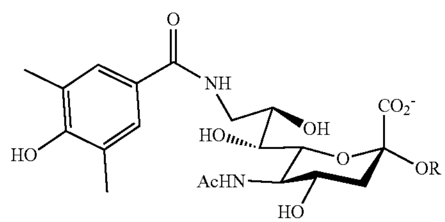 |

TABLE 1-continued
| Examples of Siglec Ligands |
| --- |
| 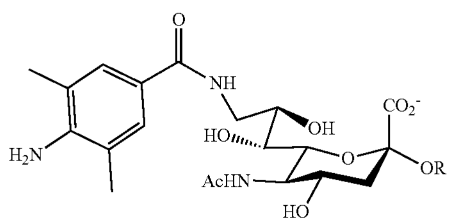 |
| 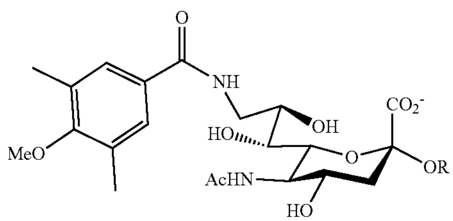 |
| 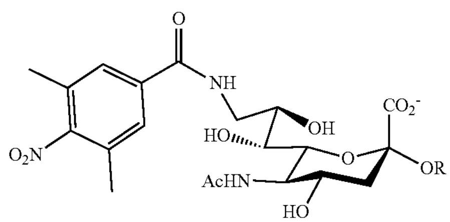 |
| 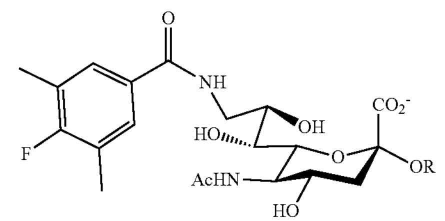 |
| 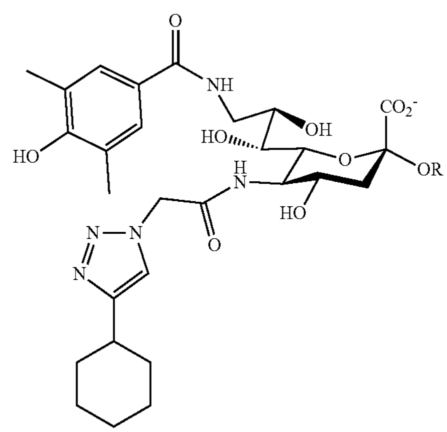 |
| 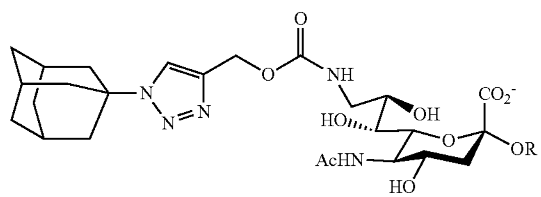 |
TABLE 1-continued
| Examples of Siglec Ligands |
| --- |
| 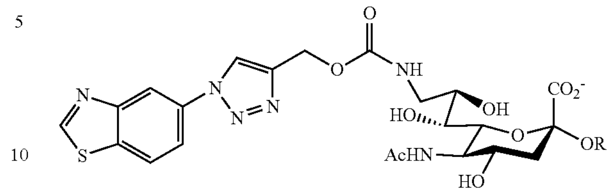 |
| 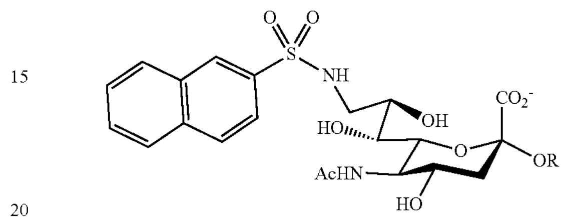 |
| 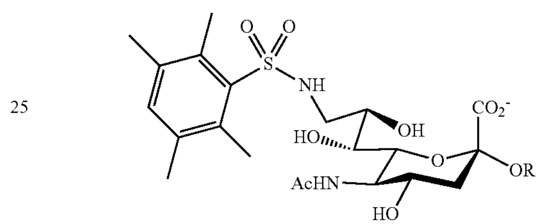 |
| 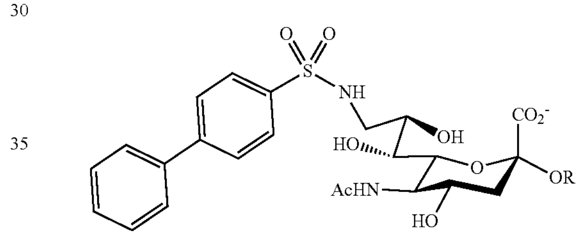 |
| 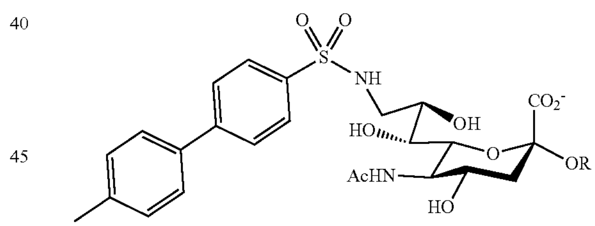 |
| 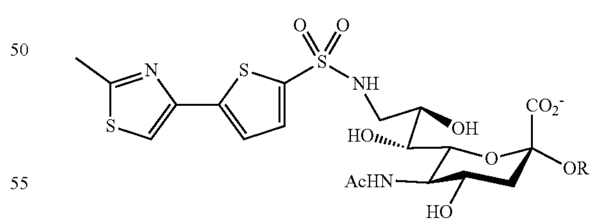 |
| 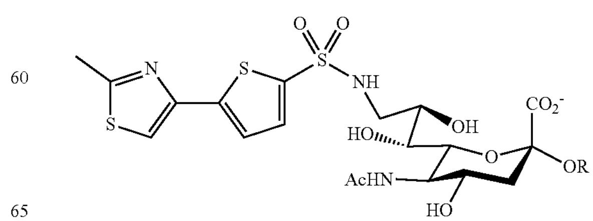 |

TABLE 1-continued

| Examples of Siglec Ligands |
| --- |
| 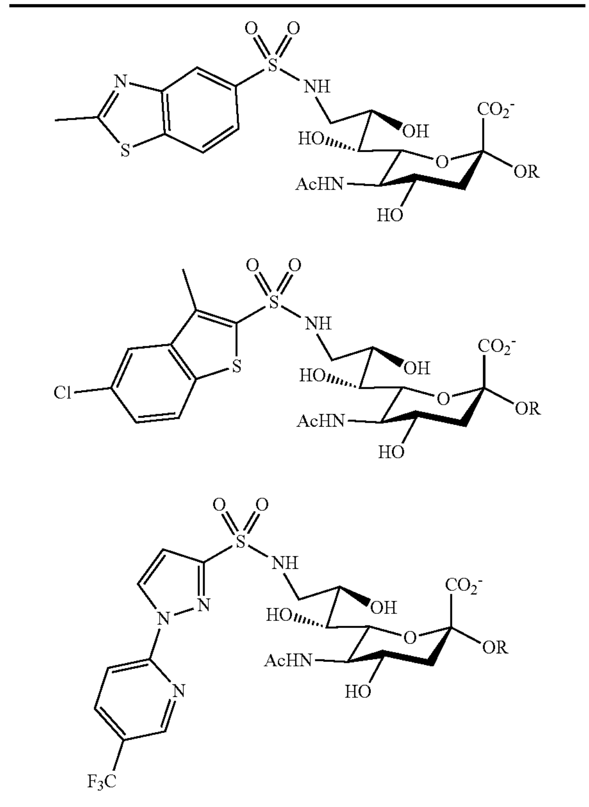 |

Conjugates

One or more of the Siglec ligands can be conjugated to antibodies. However, the number of Siglec ligands conjugated to antibodies can influence the effectiveness of immune suppression. For example, in some cases, conjugation of just one Siglec ligand to an antibody is not sufficient for effective immune suppression. Instead, the antibody should be conjugated to more than one, or more than two, or more than three, or more than four, or more than five, or more than six, or more than seven, or more than eight, or more than nine, or more than ten, or more than eleven, or more than twelve, or more than thirteen, or more than fourteen, or more than fifteen, or more than seventeen, or more than twenty, or more than twenty or more than thirty, or more than forty, or more than fifty, or more than sixty, or more than 80 Siglec ligands.

The Siglec ligands can be conjugated to antibodies either directly or indirectly. Direct linkage can involve conjugation of the Siglec ligand R group or $R_2$ group to an antibody. Indirect conjugation can involve use of a spacer or linker between the Siglec ligand and the antibody.

The Siglec ligands can be conjugated to antibodies by functional groups on the surface of the native antibody, or conjugated site-specifically to antibodies engineered to contain functional groups at specific sites on the antibody structure.

The general scheme for indirect conjugation of Siglec ligands to amino (—$NH_2$) groups on lysine residues the surface of the antibody is illustrated in the Scheme below:

Step I:

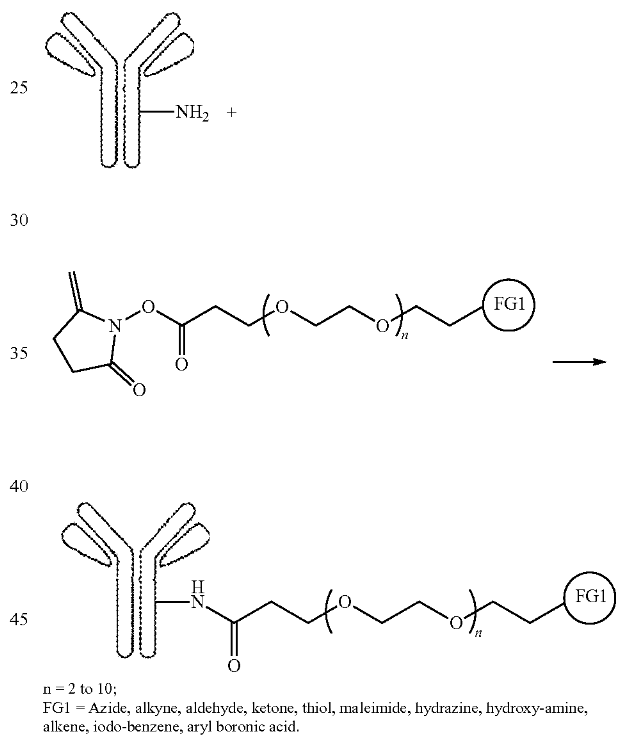

n = 2 to 10;
FG1 = Azide, alkyne, aldehyde, ketone, thiol, maleimide, hydrazine, hydroxy-amine, alkene, iodo-benzene, aryl boronic acid.

Step II:

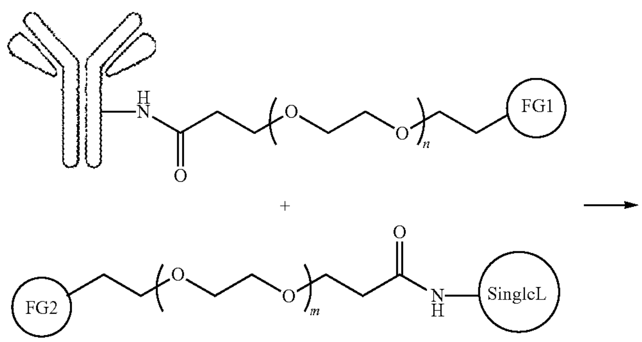

-continued

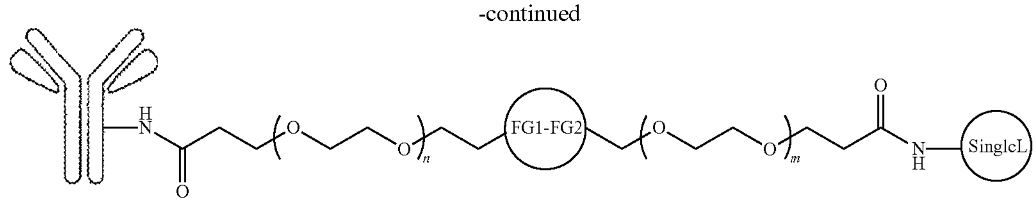

n = 2 to 10: m = 2 to 10
1. FG1 = Azide: FG2 = Alkyne
2. FG1 = Aldehyde: FG2 = Hydrazine
3. FG1 = Thiol: FG2 = Maleimide
4. FG1 = Alkene: FG2 = Iodobenzene, Aryl boronic acid
5. FG1 = Ketone: FG2 = Alkoxy-amine In this indirect approach, a lysine amino group of the anti-receptor antibody can be conjugated with NHS-Peg$_{2-10}$-FG1, where functional group 1 (FG1) can be azido, alkyne, thiol, aldehyde, ketone, maleimide, hydrazine, hydroxy amine, alkene, aryl-iodide, aryl-boronic acid, as illustrated in Step 1. This is then followed by addition of orthogonal FG2-Peg$_{2-10}$-Siglec ligand (where functional group 2 (FG2) can be azido, alkyne, thiol, aldehyde, ketone, maleimide, hydrazine, hydroxy amine, alkene, aryl-iodide, aryl-boronic acid chosen to be reactive with FG1 as illustrated in Step 2.

Alternatively, a recombinant anti-receptor antibody can be engineered to generate functional groups that will allow introduction of FG1 that can then be conjugated to Siglec ligand using generate with FG1 in site specific way and FG1 can be conjugated with orthogonal FG2-Peg$_{2-10}$-Siglec ligand (Akkapeddi P, Azizi S A, Freedy A M, Cal P, Gois P M P, and Bernardes G J L. Construction of homogeneous antibody-drug conjugates using site-selective protein chemistry. *Chemical science.* 2016; 7(5):2954-63; Sochaj A M, Swiderska K W, and Otlewski J. Current methods for the synthesis of homogeneous antibody-drug conjugates. *Biotechnology advances.* 2015; 33(6 Pt 1):775-84). An alternative to adding functional groups to the polypeptide is to add functional groups to native N-linked glycans on the antibody, or glycans engineered into a recombinant antibody, examples, for glycoengineering of Fc-N glycans or recombinant Fab-N glycans of antibody to introduce functional groups that can facilitate direct or indirect conjugation of Siglec ligands to antibody are reviewed (Tang F, Wang L X, and Huang W. Chemoenzymatic synthesis of glycoengineered IgG antibodies and glycosite-specific antibody-drug conjugates. *Nature protocols.* 2017; 12(8):1702-21; Iliott S, Chang D, Delorme E, Eris T, and Lorenzini T. Structural requirements for additional N-linked carbohydrate on recombinant human erythropoietin. *The Journal of biological chemistry.* 2004; 279(16):16854-62).

Treatment

The compositions described herein can be administered to treat subjects, such as animals or humans in need of such treatment, or who may develop a need for such treatment. For example, the compositions can reduce the incidence and severity of immune system-related disorders or diseases. Examples of immune system-related disorders or diseases that can be treated include allergic rhinitis, allergic asthma, non-allergic asthma, atopic dermatitis, allergic gastroenteropathy, anaphylaxis, urticaria, food allergies, allergic bronchopulmonary aspergillosis, parasitic diseases, interstitial cystitis, hyper-IgE syndrome, ataxia-telangiectasia, Wiskott-Aldrich syndrome, athymic lymphoplasia, IgE myeloma, graft-versus-host reaction, allergic purpura, rheumatoid arthritis, ulcerative colitis, crones disease, immune thrombocytopenia (ITP), thrombotic thrombocytopenic purpura (TTP).

In some cases, the disease or condition is an IgE-related disease or condition.

Animals including humans, domesticated animals, zoo animals, and experimental animals can be administered the compositions.

Administration of the compositions described herein can reduce the incidence of antigen-specific mast cell, eosinophil, or basophil degranulation by at least 10%, or at least 20%, or at least 25%, or at least 30%, or at least 35%, or at least 40%, or at least 45%, or at least 50%, or at least 55%, or at least 60%, or at least 65%, or at least 70%, or at least 80%, at least 90%, at least 92%, at least 95%, at least 97%, at least 98%, or at least 99%. In some cases, the compositions describe herein can reduce the symptoms and/or incidence of antigen-specific mast cell, eosinophil degranulation, or basophil degranulation by 100%.

Dosages, Formulations and Routes of Administration

The compositions described herein can include at least at least one Siglec ligand-antibody conjugate. The compositions described herein can be used to modulate an immune response (e.g., suppress, inhibit, direct, or redirect). In some embodiments, the compositions can include at least one Siglec-2, Siglec-3, and/or Siglec-8 glycan ligand conjugated to an antibody. The antibody can be an anti-receptor antibody. The anti-receptor antibody can bind to a receptor or receptor complex that normally activates the cell, such as the IgD B cell receptor, or IgM B cell receptor, or an IgE/FcεRI receptor complex on a mast cell. The compositions can optionally include another immunomodulatory agent.

Compositions described herein can be administered so as to ameliorate one or more symptoms of an immune related disease or condition. Such immune-related diseases include diseases involving over-active immune responses.

For example, the compositions can inhibit mast cell, basophil, eosinophil, or B cell activation and/or degranulation. In some embodiments, the compositions can be administered so as to achieve a reduction in at least one symptom associated with an IgE-mediated disorder or disease. Examples of IgE-mediated disorders or diseases include allergic rhinitis, allergic asthma, non-allergic asthma, atopic dermatitis, allergic gastroenteropathy, anaphylaxis, urticaria, food allergies, allergic bronchopulmonary aspergillosis, parasitic diseases, interstitial cystitis, hyper-IgE syndrome, ataxia-telangiectasia, Wiskott-Aldrich syndrome, athymic lymphoplasia, IgE myeloma, graft-versus-host reaction and allergic purpura.

To achieve the desired effect(s), one or more of the Siglec ligand-antibody conjugates may be administered in single or divided dosages.

For example, the Siglec ligand-antibody conjugates can be present in the compositions in amounts of at least about 0.01 mg/kg to about 100 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results.

The amount administered will vary depending on various factors including, but not limited to, what types of Siglec ligand-antibody conjugates, and/or other therapeutic agents are administered, the route of administration, the progression or lack of progression of the disease, the weight, the physical condition, the health, the age of the patient, whether prevention or treatment is to be achieved, and if the antigen or ligand is chemically modified. Such factors can be readily determined by the clinician employing animal models or other test systems that are available in the art.

Siglec ligand-conjugates may be administered in a single dose, in multiple doses, in a continuous or intermittent manner, depending, for example, upon the recipient's physiological condition, whether the purpose of the administration is therapeutic or prophylactic, and other factors known to skilled practitioners. The administration of the compositions may be essentially continuous over a pre-selected period of time or may be in a series of spaced doses. Both local and systemic administration is contemplated.

To prepare the composition, the Siglec ligand-conjugates are synthesized or otherwise obtained and purified as necessary or desired. These therapeutic agents can then be lyophilized or stabilized, for example, if storage is desirable. The concentrations of the therapeutic agents can be evaluated and adjusted to an appropriate amount, and optionally combined with other active agents.

In general, dosage forms of the invention comprise an amount of at least one of the Siglec ligand-conjugates effective to treat or prevent the clinical symptoms of a disease (e.g. an immune related disease). Any statistically significant attenuation of one or more symptoms of an immune-related disorder or disease is considered to be a treatment thereof.

The absolute weight of a given Siglec ligand-conjugate that is included in a unit dose can vary widely. For example, about 0.01 to about 2 g, or about 0.1 to about 500 mg, of at least one Siglec ligand-conjugate can be administered. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

Daily doses of a Siglec ligand-conjugates can vary as well. Such daily doses can range, for example, from about 0.1 g/day to about 50 g/day, from about 0.1 g/day to about 25 g/day, from about 0.1 g/day to about 12 g/day, from about 0.5 g/day to about 8 g/day, from about 0.5 g/day to about 4 g/day, and from about 0.5 g/day to about 2 g/day.

The compositions that include active ingredients including the Siglec ligand-antibody conjugates described herein can include a carrier such as a pharmaceutically acceptable carrier. By "pharmaceutically acceptable" it is meant a pharmaceutical carrier, diluent, excipient, and/or salt that is compatible with the other ingredients of the formulation, and not deleterious to the recipient thereof. A "pharmaceutically acceptable carrier" or a "pharmaceutical carrier" is a non-active ingredient that is not deleterious to the recipient thereof and that can solubilize or disperse the active ingredients to facilitate formulation of a convenient dosage form.

One or more suitable unit dosage forms comprising the therapeutic agents of the invention can be administered by a variety of routes including parenteral (including subcutaneous, intravenous, intramuscular and intraperitoneal), oral, rectal, dermal, transdermal, intrathoracic, intrapulmonary and intranasal (respiratory) routes. The therapeutic agents may also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing the therapeutic agent with liquid solutions, solid matrices, semi-solid pharmaceutical carriers, finely divided solid pharmaceutical carriers or combinations thereof, and then, if necessary, introducing or shaping the product into the desired delivery system.

Pharmaceutical formulations containing the therapeutic agents described herein can be prepared by available procedures using available ingredients. The formulations can contain pharmaceutically acceptable carriers, vehicles and adjuvants. For example, the therapeutic agents can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive pharmaceutical carriers such as kaolin and bentonite can be added. Lubricants such as talc, calcium and magnesium stearate, and solid polyethylene glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

It is possible, for example, to prepare solutions using one or more aqueous or organic solvent(s) that is/are acceptable from the physiological standpoint, chosen, in addition to water, from solvents such as acetone, ethanol, isopropyl alcohol, glycol ethers such as the products sold under the name "Dowanol," polyglycols and polyethylene glycols, $C_1$-$C_4$ alkyl esters of short-chain acids, ethyl or isopropyl lactate, fatty acid triglycerides such as the products marketed under the name "Miglyol," isopropyl myristate, animal, mineral and vegetable oils and polysiloxanes.

The therapeutic agents may be formulated for parenteral administration (e.g., by injection, for example, bolus injection or continuous infusion) and may be presented in unit dose form in ampoules, pre-filled syringes, small volume infusion containers or in multi-dose containers. The administration can, for example, be subcutaneous, or intravenous.

As noted above, preservatives can be added to help maintain the shelve life of the dosage form. The active agents and other ingredients may form suspensions, solutions, or emulsions in oily or aqueous vehicles, and may contain formulatory agents such as suspending, stabilizing and/or dispersing agents. Alternatively, the therapeutic agents and other ingredients may be in powder form, obtained by aseptic isolation of sterile solid or by lyophilization from solution, for constitution with a suitable vehicle, e.g., sterile, pyrogen-free water, before use.

When the therapeutic agents of the invention are prepared for oral administration, they are generally combined with a pharmaceutically acceptable carrier, diluent or excipient to form a pharmaceutical formulation, or unit dosage form. For oral administration, the therapeutic agents may be present as a powder, a granular formulation, a solution, a suspension, an emulsion or in a natural or synthetic polymer or resin for ingestion of the active ingredients from a chewing gum. The therapeutic agents may also be presented as a bolus, electuary or paste.

When the compositions are prepared for, and administered as, oral compositions, they can, for example, be prepared as tablets or caplets. The compositions containing the therapeutic agents (Siglec ligands-antibody conjugates) can include buffering agents such as calcium carbonate, magnesium oxide and magnesium carbonate. Caplets and tablets can also include inactive ingredients such as cellulose, pre-gelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatin capsules containing at least one therapeutic agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric-coated caplets or tablets containing one or more of the therapeutic agents of the invention are designed to resist disintegration in the stomach and dissolve in the more neutral to alkaline environment of the duodenum.

Orally administered therapeutic agents of the invention can also be formulated for sustained release. For example, the therapeutic agents can be coated, micro-encapsulated, or otherwise placed within a sustained delivery device. The total active ingredients in such formulations comprise from 0.1 to 99.9% by weight of the formulation.

The therapeutic agents of the invention can also be formulated as elixirs or solutions for convenient oral administration or as solutions appropriate for parenteral administration, for instance by intramuscular, subcutaneous, intraperitoneal or intravenous routes. The pharmaceutical formulations of the therapeutic agents of the invention can also take the form of an aqueous or anhydrous solution or dispersion, or alternatively the form of an emulsion or suspension or salve.

The compositions can also include antioxidants, surfactants, preservatives, film-forming, keratolytic or comedolytic agents, perfumes, flavorings and colorings. Antioxidants such as t-butylhydroquinone, butylated hydroxyanisole, butylated hydroxytoluene and α-tocopherol and its derivatives can be added.

Additionally, the therapeutic agents are suited to formulation as sustained release dosage forms and the like. The formulations can be so constituted that they release the active agent, for example, in a localized or systemic manner optionally over a period of time. In some cases, the formulations can be so constituted for release in the vascular system or respiratory tract, Coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, catheters, peritoneal dialysis tubing, draining devices and the like.

For topical administration, the therapeutic agents may be formulated by available methods for direct application to a target area. Forms chiefly conditioned for topical application take the form, for example, of creams, milks, gels, dispersion or microemulsions, lotions thickened to a greater or lesser extent, impregnated pads, ointments or sticks, aerosol formulations (e.g., sprays or foams), soaps, detergents, lotions or cakes of soap. Other conventional forms for this purpose include wound dressings, coated bandages or other polymer coverings, ointments, creams, lotions, pastes, jellies, sprays, and aerosols.

The compositions can be delivered via patches or bandages for dermal administration. Alternatively, the therapeutic agents can be formulated to be part of an adhesive polymer, such as polyacrylate or acrylate/vinyl acetate copolymer. For long-term applications it might be desirable to use microporous and/or breathable backing laminates, so hydration or maceration of the skin can be minimized. The backing layer can be any appropriate thickness that will provide the desired protective and support functions. A suitable thickness will generally be from about 10 to about 200 microns.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. Nos. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1-85% by weight.

Drops, such as eye drops or nose drops, may be formulated with one or more of the therapeutic agents in an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The therapeutic agents may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid pharmaceutical carrier.

The compositions may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the pharmaceutical carriers and/or diluents that are useful in the pharmaceutical formulations of the present invention include water and physiologically acceptable buffered saline solutions such as phosphate buffered saline solutions pH 7.0-8.0.

The active ingredients of the invention can also be administered to the respiratory tract. Thus, the present invention also provides aerosol pharmaceutical formulations and dosage forms for use in the methods of the invention.

For administration by inhalation or insufflation, the composition may be in the form of a dry powder, for example, a powder mix of the therapeutic agent and a suitable powder base such as lactose or starch. The powder composition may be presented in unit dosage form in, for example, capsules or cartridges, or, e.g., gelatin or blister packs from which the powder may be administered with the aid of an inhalator, insufflator, or a metered-dose inhaler (see, for example, the pressurized metered dose inhaler (MDI) and the dry powder inhaler disclosed in Newman, S. P. in *Aerosols and the Lung*, Clarke, S. W. and Davia, D. eds., pp. 197-224, Butterworths, London, England, 1984).

Therapeutic agents of the present invention can also be administered in an aqueous solution when administered in an aerosol or inhaled form. Thus, other aerosol pharmaceutical formulations may comprise, for example, a physiologically acceptable buffered saline solution containing between about 0.1 mg/ml and about 100 mg/ml of one or more of the therapeutic agents of the present invention specific for the indication or disease to be treated. Dry aerosol in the form of finely divided solid therapeutic agent that are not dissolved or suspended in a liquid are also useful in the practice of the present invention. Therapeutic agents of the present invention may be formulated as dusting powders and comprise finely divided particles having an average particle size of between about 1 and 5 μm, alternatively between 2 and 3 μm. Finely divided particles may be prepared by pulverization and screen filtration using techniques well known in the art. The particles may be administered by inhaling a predetermined quantity of the finely divided material, which can be in the form of a powder.

It will be appreciated that the unit content of active ingredient or ingredients contained in an individual aerosol dose of each dosage form need not in itself constitute an effective amount for treating the particular immune response, allergy, asthma, anaphylaxis or other disease or condition since the necessary effective amount can be reached by administration of a plurality of dosage units. Moreover, the effective amount may be achieved using less than the dose in the dosage form, either individually, or in a series of administrations.

For administration to the upper (nasal) or lower respiratory tract by inhalation, the therapeutic agents of the invention are conveniently delivered from a nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Nebulizers include, but are not limited to, those described in U.S. Pat. Nos. 4,624,251; 3,703,173; 3,561,444; and 4,635,627. Aerosol delivery systems of the type disclosed herein are available from numerous commercial sources including Fisons Corporation (Bedford, Mass.), Schering Corp. (Kenilworth, NJ) and American Pharmoseal Co., (Valencia, CA). For intra-nasal administration, the therapeutic agent may also be administered via nose drops, a liquid spray, such as via a plastic bottle atomizer or metered-dose inhaler. Typical of atomizers are the Mistometer (Wintrop) and the Medihaler (Riker).

Furthermore, the active ingredients may also be used in combination with other therapeutic agents, for example, pain relievers, anti-inflammatory agents, anti-cancer agents and the like, whether for the conditions described or some other condition.

Kits

The present invention further pertains to a packaged pharmaceutical composition such as a kit or other container for detecting, controlling, preventing or treating a disease. The kits of the invention can be designed for detecting, controlling, preventing or treating immune responses, immune conditions, and autoimmune diseases such as those described herein (e.g., an allergy, anaphylaxis).

In one embodiment, the kit or container holds a Siglec ligand-antibody conjugate for inhibiting immune responses, as well as instructions for preparing a composition that includes the Siglec ligand-antibody conjugate.

In another embodiment, the kit or container holds a therapeutically effective amount of a pharmaceutical composition for treating, preventing or controlling a disease and instructions for using the pharmaceutical composition for control of the disease. The pharmaceutical composition includes at least one types of Siglec ligand-antibody conjugate in a therapeutically effective amount such that the disease is controlled, prevented or treated. Such a composition can be in liquid form, powder form or other form permitting ready administration to a patient.

The kits of the invention can also comprise containers with tools useful for administering the compositions of the invention. Such tools include syringes, swabs, catheters, antiseptic solutions and the like.

Definitions

Aryl groups are cyclic aromatic hydrocarbons that do not contain heteroatoms. An aryl group can have about five to about fourteen ring atoms in which at least one ring is aromatic. Examples include a phenyl ring, a bicyclic ring (e.g., biphenyl), or tricyclic ring. Bicyclic and tricyclic rings can be ortho-fused but, as used herein, the bicyclic and tricyclic rings need not be fused and can be separate rings linked together by a covalent bond or a short alkyl (e.g. $C_1$-$C_3$ alkyl). Examples of aromatic groups include groups such as benzene, phenyl, biphenyl, naphthalene, anthracene, or a combination thereof.

Thus, aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Heterocyclic or heterocycle groups include aromatic and non-aromatic ring compounds containing three or more ring atoms, of which, one or more is a heteroatom such as, but not limited to, N, O, and S. The heteroatom can, for example, be a nitrogen atom. In some embodiments, heterocycle groups include 3 to about 20 ring atoms, whereas other such groups have 3 to about 15 ring atoms. A heterocycle group designated as a $C_2$-heterocyclyl can be a 5-ring with two carbon atoms and three heteroatoms, a 6-ring with two carbon atoms and four heteroatoms and so forth. Likewise, a $C_4$-heterocyclyl can be a 5-ring with one heteroatom, a 6-ring with two heteroatoms, and so forth. The number of carbon atoms plus the number of heteroatoms sums up to equal the total number of ring atoms. A heterocycle ring can also include one or more double bonds. A heteroaryl ring is an embodiment of a heterocycle group. The phrase "heterocycle group" includes fused ring species including those comprising fused aromatic and non-aromatic groups. For example, a dioxolanyl ring and a benzodioxolanyl ring system (methylenedioxyphenyl ring system) are both heterocycle groups within the meaning herein. The phrase also includes polycyclic ring systems containing a heteroatom such as, but not limited to, quinuclidyl. Heterocyclic groups can be unsubstituted, or heterocyclic groups can be substituted as discussed above. Heterocyclic groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocycle groups can be mono-substituted or substituted more than once, such as, but not limited to, piperidinyl or quinolinyl groups, which are 2-, 3-, 4-, 5-, or 6-substituted, or disubstituted with groups such as those listed above.

In some embodiments, the heterocyclic ring is a non-aromatic ring with one or two heteroatoms. For example, the heterocyclic ring can be a non-aromatic ring with one heteroatom. The heteroatom can, for example, be oxygen, sulfur, or nitrogen.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, isobutyl, sec-butyl, t-butyl, neopentyl, isopentyl, and 2,2-dimethylpropyl groups. Lower alkyl groups have about 1 to about 3 carbon atoms.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein. A lower alkoxy group has about 1 to about 3 carbon atoms.

An "amino" group is a substituent of the form $—NH_2$, —NHR, $—NR_2$, $—NR_3^+$, and protonated forms of each, wherein each R is independently selected from a hydrogen or a lower alkyl group.

"Halogen" or "halo" as the term is used herein includes fluoro, chloro, bromo, and iodo.

All chiral, diastereomeric, racemic forms of a structure are intended to be embraced by the claims, unless the specific stereochemistry or isomeric form is specifically indicated. Compounds used in the present invention include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these are all within the scope of the invention.

The following examples are for illustration of certain aspects of the invention and is not intended to be limiting thereof.

Example 1: Illustrates the Impact of Siglec Ligands Conjugated to Antibodies Upon Immune Cell Activitory Receptors on B Cells and Mast Cells This Example describes various types Siglec ligands conjugated to antibodies to immune cell activitory receptors and illustrates the impact of such Siglec ligand-antibody conjugates.

FIG. 1A is a schematic illustrating activation of a B cell as induced by an anti-IgD B cell receptor (anti-IgD BCR) antibody. However, FIG. 1B shows that such activation is suppressed when the anti-IgD antibody is conjugated to a CD22 ligand (CD22L) because CD22 is recruited to the IgD BCR.

FIG. 1C is a schematic illustrating activation of a mast cell when anti-IgE antibodies ligate to an IgE/FcεRI complex on the mast cell. However, when the anti-IgE antibody is conjugated to a CD33 ligand (CD33L), activation and degranulation of the mast cell is suppressed as a result of the inhibitory CD33 being recruited to the IgE/FcεR1 receptor complex (FIG. 1D).

Example 2: Synthetic High Affinity Siglec Ligands
The following are examples of ligands for various Siglecs. For example, the following are examples of Siglec ligands for CD33.
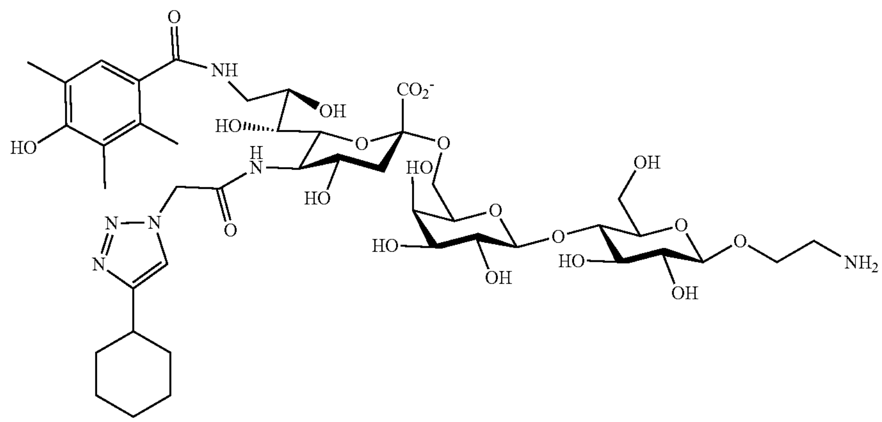
CD33L
The following are examples of Siglec ligands for mouse and human CD22 (mCD22L and CD22L, respectively).
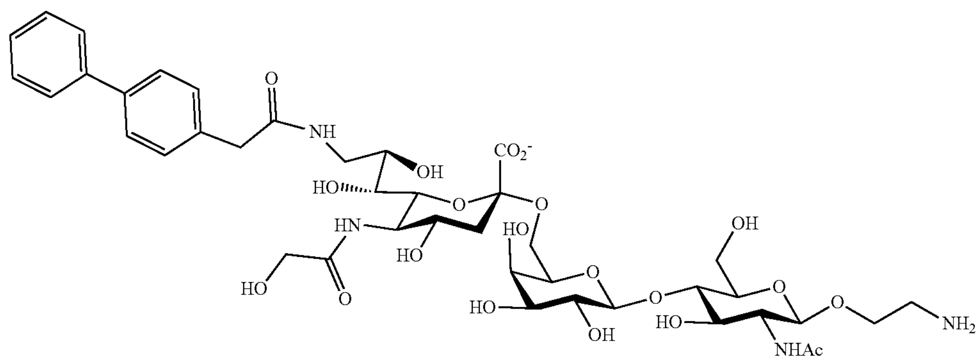
mCD22L
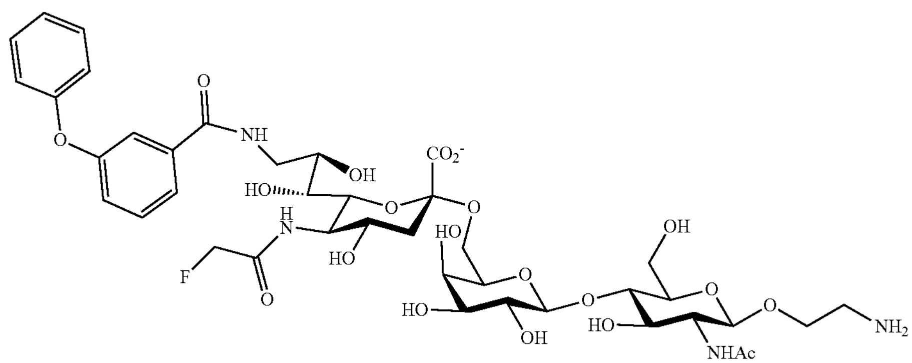
CD22L Example 3: Conjugation of High Affinity Siglec Ligands to Antibodies This Example illustrates methods for conjugating Siglec ligands to antibodies.

Figure 2B:
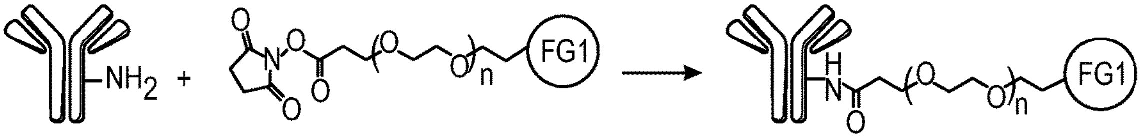
Figure 2B:
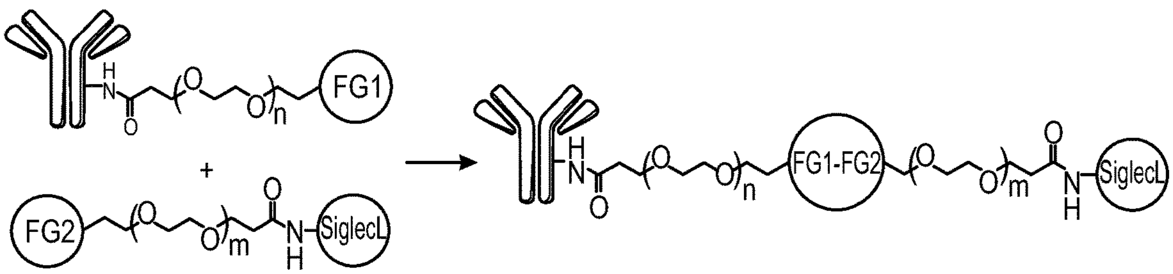

FIG. 2B shows a general scheme for indirect conjugation of Siglec ligands to amino (—$NH_2$) groups on lysine residues the surface of an antibody, where n is 2 to 10. In step 1, functional group 1 (FG1) can be an azide, alkyne, aldehyde, ketone, thiol, maleimide, hydrazine, hydroxyamine, alkene, iodo-benzene, or aryl boronic acid. In step 2, various functional groups can be used for FG1 and FG2. For example, FG1 can be azide while FG2 can be alkyne; or FG1 can be aldehyde while FG2 can be hydrazine; or FG1 can be thiol while FG2 can be maleimide; or FG1 can be alkene while FG2 can be Iodobenzene or aryl boronic acid; or FG1 can be ketone while FG2 can be alkoxy-amine.

Figure 3A:
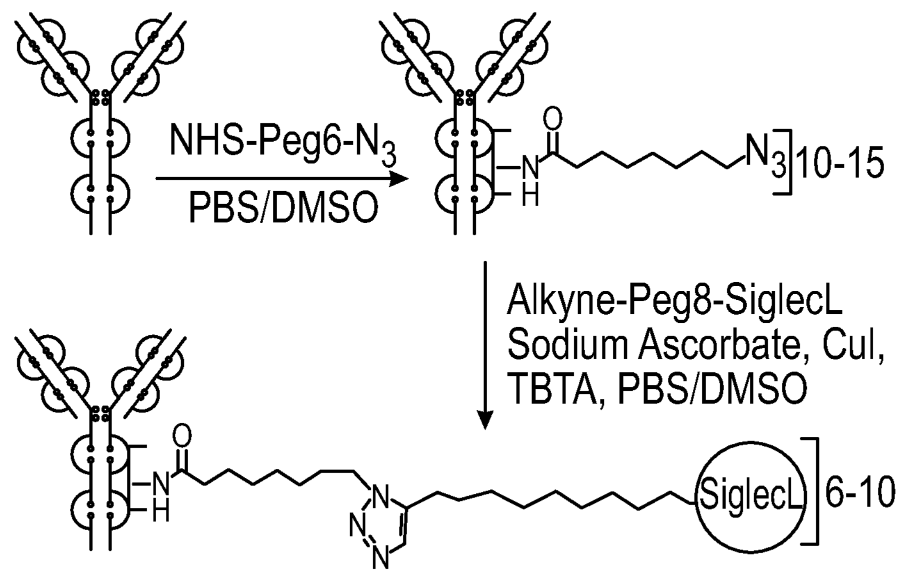
FIG. 3A-3C illustrate methods for conjugation of synthetic high affinity Siglec ligands to antibodies.

As shown in FIG. 3A, several copies of an NHS-ester functionalized PEG linker (NHS-Peg-$N_3$) can be covalently linked to various amino acids of an antibody. The one or more amino acids of the antibody can serve as the linker conjugation site when they are not involved in antigen binding (e.g. not CDR amino acids) and are not involved in antibody communication with other components of the immune system (e.g., not key amino acids in the Fc region). An antibody was treated with NHS-Peg6-N3 in PBS and DMSO to covalently attach 10-15 functionalized linkers to various lysine residues as illustrated at the top of FIG. 3A.

The distal functionalized ends of the linkers were then covalently bonded to the Siglec ligand (see reaction illustrated in FIG. 3A). Briefly, an alkyne-PEGS functionalized Siglec ligand was reacted with the antibody-functionalized linker in the presence of sodium ascorbate, copper(I)-iodide (CuI), and tris(benzyltriazolyl)methyl amine. This reaction can provide antibody-Siglec ligand conjugates where the antibodies have about 6-10 covalently attached Siglec ligands per antibody.

Figure 3B:
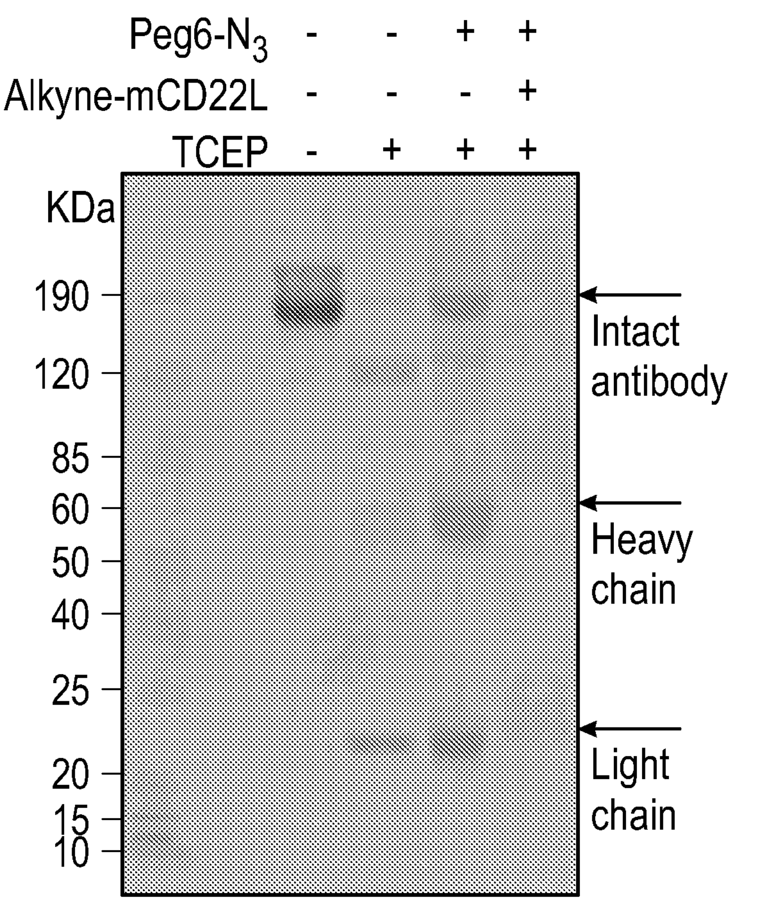
Figure 3C:
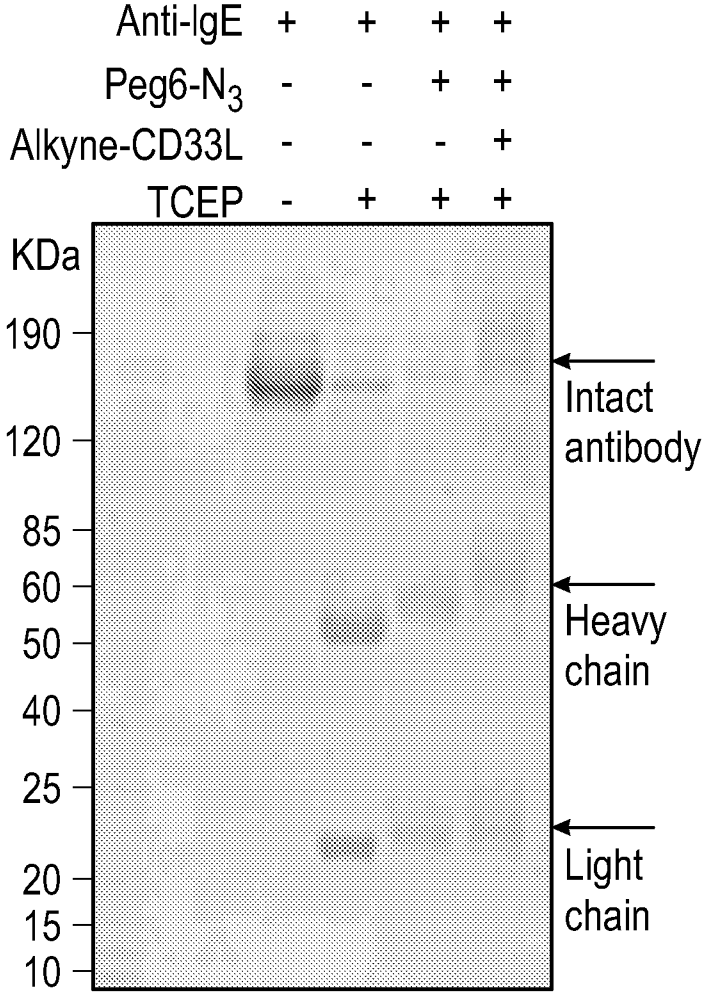

The products of the conjugation reaction were treated with TCEP (Tris 2-carboxyethyl phosphine hydrochloride) to reduce the disulfide bonds of the antibody, thereby generating heavy (MW 50-60 KDa) and light (22-25 KDa) antibody chains. FIG. 3B shows the products of the conjugation reaction between anti-IgD antibodies and a mouse CD22 ligand (mCD22L) shown in FIG. 2A as analyzed by SDS-polyacrylamide gel electrophoresis. FIG. 3C shows the products of the conjugation reaction between anti-IgE antibodies and a human CD33 ligand (CD33L) shown in FIG. 2A that were analyzed by SDS-polyacrylamide gel electrophoresis.

Example 4: CD22 Ligand-Anti-IgD Conjugates Reduce Activation of B Cells

This Example illustrates that CD22 ligand-anti-IgD conjugates can reduce activation of murine B cells.

Mouse CD22 ligands (Example 2) were conjugated to anti-IgD antibodies as described in Example 3 to form the mCD22L-anti-IgD conjugate.

Calcium flux was used as a measure of B cell activation. Calcium flux was measured using Indo-1 (Invitrogen), a calcium binding dye. Calcium flux assay was performed using splenocytes of WT BALB/cByJ and CD22KO Hy10 C57BL/6J mice and calcium flux was measured using kinetic parameter by flowjo. B cells (100 k cells/per group) were treated with anti-IgD (10 μg/ml) with or without mCD22L and N3 linker. PBS was used as a negative control.

Figure 4A:
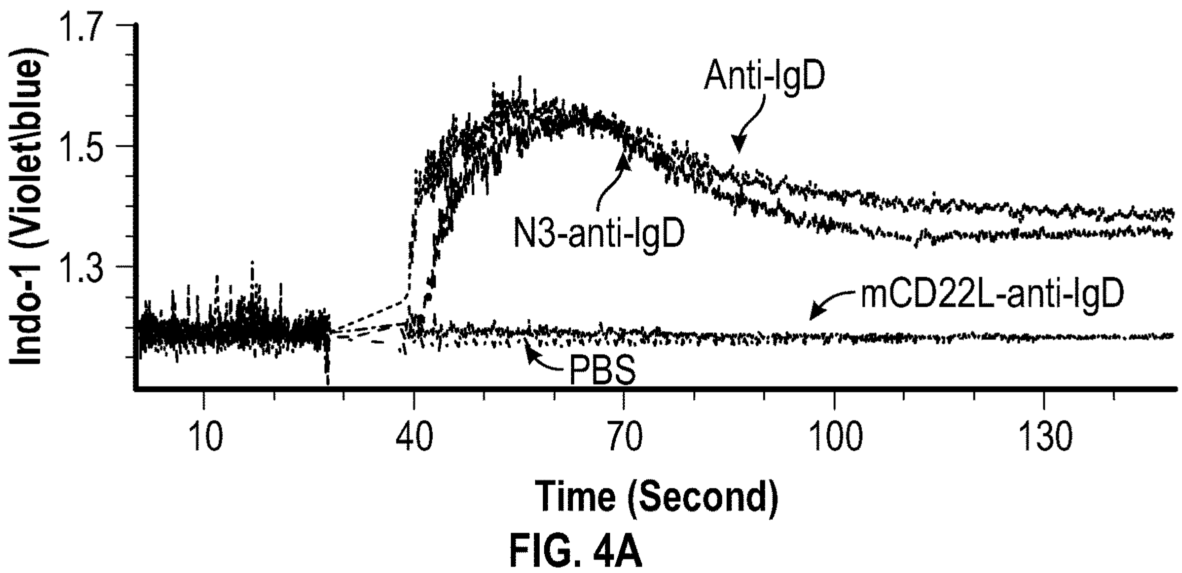
FIG. 4A-4B illustrates the impact of conjugated mCD22 ligand on anti-IgD antibody activation of murine B cells as measured by calcium flux.
Figure 4B:
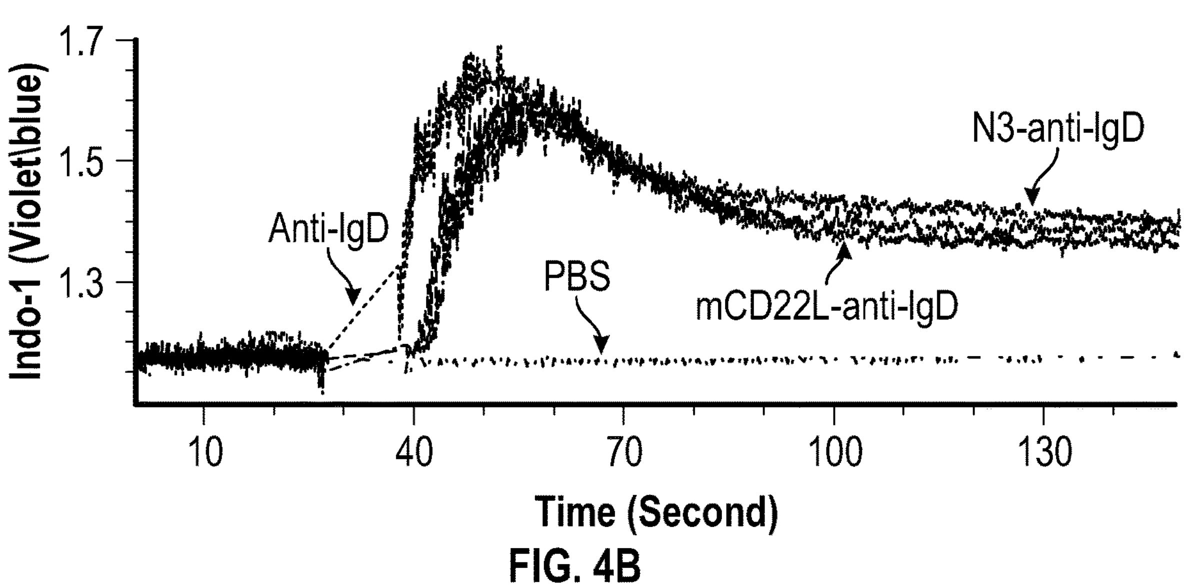

As shown in FIG. 4A, the mCD22L-anti-IgD conjugates suppressed calcium flux in splenocytes from WT BALB/cByJ mice. However, FIG. 4B shows that in mice without CD22 (CD22 knockout, CD22KO mice), no such calcium flux was inhibited. Hence, the mCD22L-anti-IgD in CD22KO Hy10 C57BL/6J mice does not inhibit calcium flux (FIG. 4B).

Example 5: Conjugation of CD33 Siglec Ligands to Anti-IgE Antibodies Reduced Mast Cell Activation and Production of IL-6

This Example describes reduction of mast cell activation by conjugates of CD33 Siglec ligands and anti-IgE antibodies.

In a first experiment, anti-IgE antibodies obtained from various sources were evaluated for induction of mast cell activation and IL-6 production. Bone marrow derived mast cells (BMMCs) were pre-sensitized overnight at 37° C. with human IgE antibodies directed against ovalbumin (anti-OVA-human IgE; 1 μg/100 k cells). The pre-sensitized BMMCs were then treated with the clones of anti-IgE antibodies (10 μg/100 k cells) shown in Table 2.

TABLE 2

Anti-human IgE Antibodies and Sources Thereof

| Clone/Hybridoma | Specificity | Isotype | Source | Catalogue No | Publication/Patent |
|---|---|---|---|---|---|
| MHE-18 | Human IgE | Mouse IgG1, k | Biolegend | 325502 | Balemans D, et al., Sci. Rep., 2017, 7, 13606. |
| HB-121 | Human IgE | Mouse IgG2a, kappa light chain | ATCC | E5BB3IIA2 | Hook WA, et al. 1983, Fed. Proc. 42: 713 |
| GE-1 | Human IgE | Mouse IgG2b | Millipore Sigma | SAB4200741 | Suutari TJ, et al., J Investig Allergol Clin Immunol., 2006, 16, 296. |
| G7-26 | Constant region of human IgE | Mouse IgG2a, k | BD Bioscience | 555857 | Cheng YX, et al., Clin Exp Allergy, 2006, 36, 1436. |
| G7-18 | Human IgE | Mouse IgG2a, k | BD Bioscience | 555894 | |
| RM-122 | Human IgE | Rabbit IgG | Millipore Sigma | 04-1649 | |

TABLE 2-continued

| Anti-human IgE Antibodies and Sources Thereof | | | | | |
|---|---|---|---|---|---|
| Clone/Hybridoma | Specificity | Isotype | Source | Catalogue No | Publication/Patent |
| E124.2.8 | Dε2 constant region of human IgE | Mouse IgG1 | Beckman Coulter | A40174 | |
| HB-235 | Epsilon heavy chain of human IgE | Mouse IgG1, kappa light chain | ATCC | CIA-E-4.15 | Hassner A, et al. J Immunol., 1984, 132(6), 2844 |
| HB-236 | Epsilon heavy chain of human IgE | Mouse IgG1, kappa light chain | ATCC | CIA-E-7.12 | Hassner A, et al. J Immunol., 1984, 132(6), 2844 |
| E4.15 | Human IgE | Mouse IgG1 | | | Zhang Ke, et al., J Immunol., 2017, 198, 3823 |
| E7.12 | Human IgE | Mouse IgG1 | | | Zhang Ke, et al., J Immunol., 2017, 198, 3823 |
| E5.1 | Human IgE | Mouse IgG1 | | | Zhang Ke, et al., J Immunol., 2017, 198, 3823 |
| E2.18 | Human IgE | Mouse IgG1 | | | Zhang Ke, et al., J Immunol., 2017, 198, 3823 |
| C6 | Human IgE | Mouse IgG1 | | | Zhang Ke, et al., J Immunol., 2017, 198, 3823 |
| p6.2 | Human IgE | Mouse IgG1 | | | Zhang Ke, et al., J Immunol., 2017, 198, 3823 |

IL-6 cytokine production by the anti-OVA-human IgE pre-sensitized BMMCs that had been treated with different clones of anti-IgE was then measured.

Figures 5A, 5B:
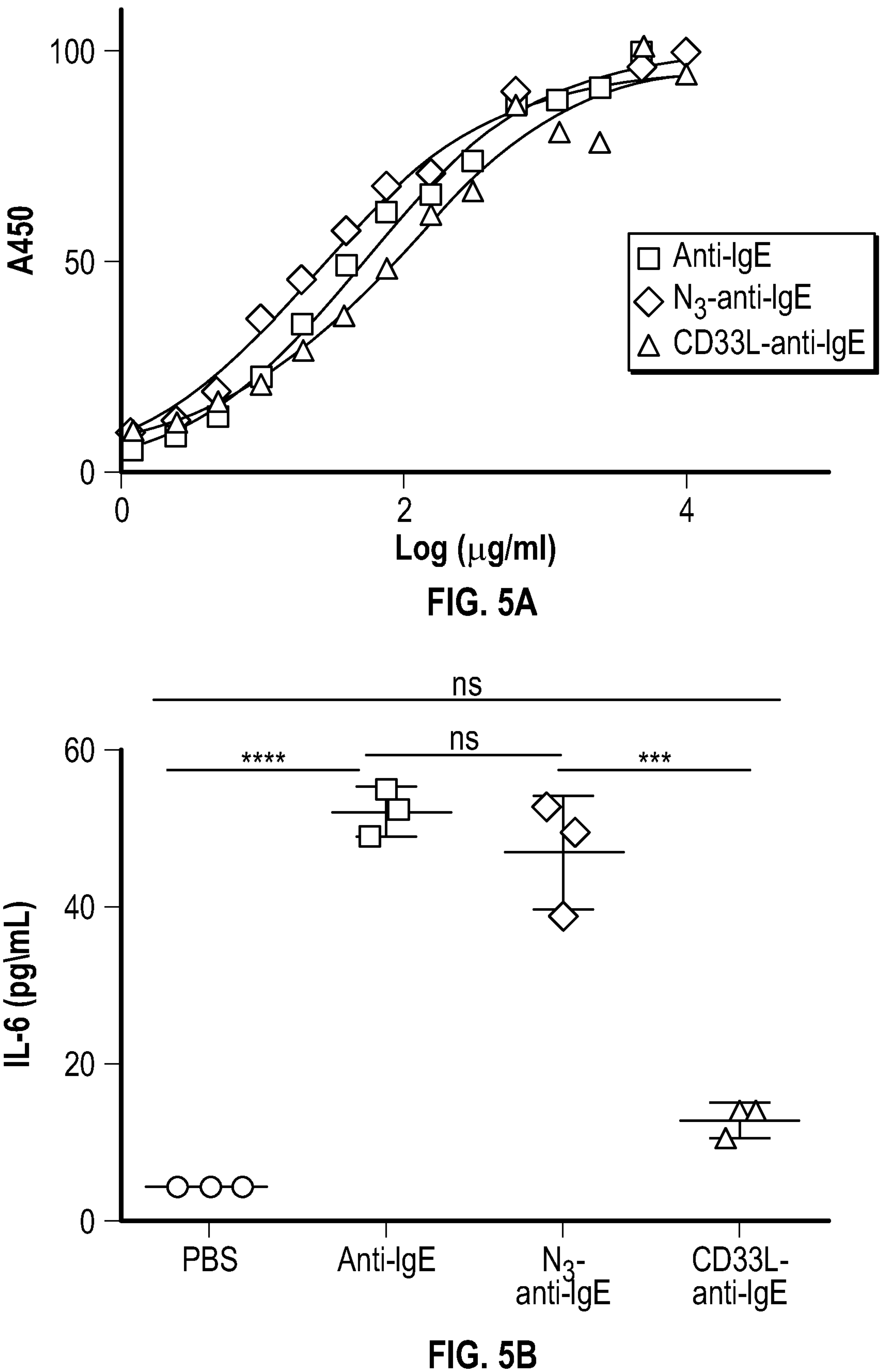
FIG. 5A-5C illustrate the impact of conjugation of CD33L to anti-IgE antibodies on binding of anti-IgE to human IgE in an ELISA assay, and the ability of anti-IgE to induce mast cell activation in mast cells by evaluating the production of the cytokine IL-6.
Figure 5C:
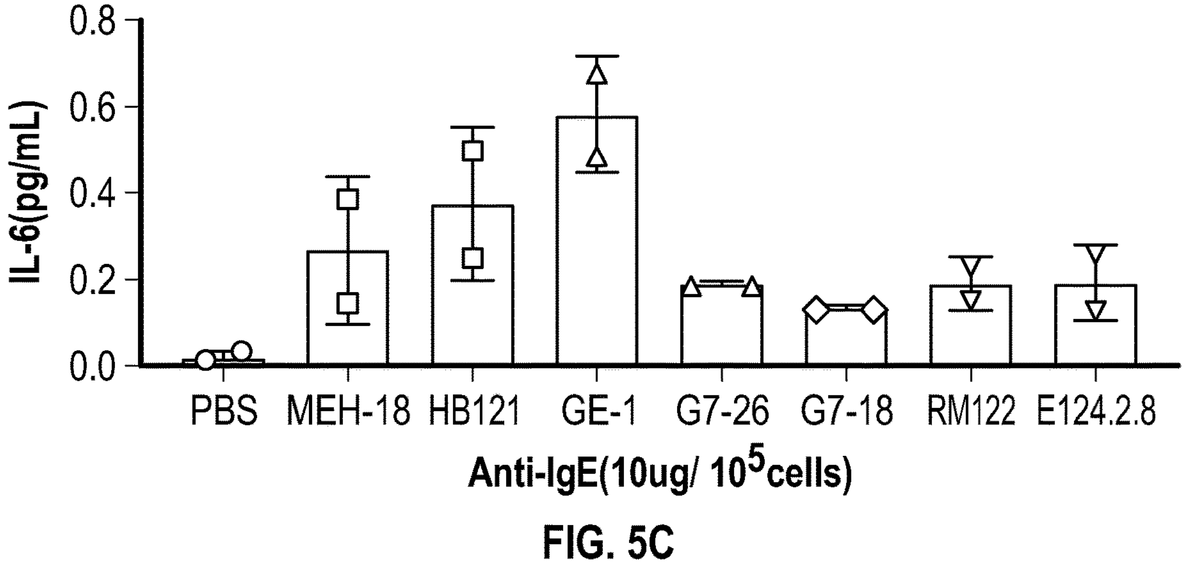

As shown in FIG. 5C, all of the anti-IgE antibodies induced the pre-sensitized BMMCs to produce IL-6 cytokines.

In another experiment, non-conjugated anti-IgE, N3-anti-IgE and CD33L-anti-IgE were compared for binding to IgE using an ELISA assay. This was done by pre-coating an ELISA plate with 1 μg/50 μl/well IgE antibodies directed against the ovalbumin antigen (anti-OVA-human IgE) overnight at 4° C. Various concentrations of non-conjugated anti-IgE, non-conjugated N3-anti-IgE, and conjugated CD33-anti-IgE were then incubated in separate reaction wells of the ELISA plate. The top concentration employed was 10 μg/100 μl/well, which was diluted by half sixteen times. Bound anti-IgE was assessed using a fluorescently labeled anti-IgE and the binding activity is compared using the effective concentration needed to achieve half maximal binding ($EC_{50}$).

Interleukin 6 (IL-6) cytokine production was measured by pre-sensitizing bone marrow derived mast cells (BMMCs) with human IgE antibodies directed to ovalbumin (anti-OVA-human IgE) using a concentration of 1 μg IgE antibodies per 100,000 cells. The antibodies and the cells were incubated overnight at 37° C. The cells were then treated with 10 μg non-conjugated anti-IgE, non-conjugated N3-anti-IgE, or CD33L-anti-IgE conjugate per 100,000 cells.

FIG. 5A shows the half-maximal effective concentration ($EC_{50}$) of CD33L-anti-IgE for binding to IgE is within a factor of 2-fold, indicating that conjugation of the anti-IgE antibodies to the CD33 ligand has little impact on the binding activity.

FIG. 5B shows that IL-6 cytokine production by bone marrow derived mast cells is significantly reduced by CD33L-anti-IgE conjugates compared to the IL-6 production by bone marrow derived mast cells incubated with non-conjugated anti-IgE or non-conjugated N3-anti-IgE.

Example 6: Treatment with CD33L-Anti-IgE Conjugates Reduces Anaphylactic Responses in Mice This Example illustrates the impact of treating mice with CD33L-anti-IgE conjugates upon induction of passive cutaneous anaphylaxis in mice.

Mice that express human CD33 and mice that do not express human CD33 were used. One ear of each mouse was pre-sensitized with anti-ovalbumin (anti-OVA) human IgE antibodies (1 μg/mice) that recognize ovalbumin antigen (anti-OVA-human IgE) followed by treatment one day later with human anti-IgE conjugated or not conjugated with the CD33 ligand (CD33L shown in Example 2 at 10 μg/mice) for one hour.

Figure 6A:
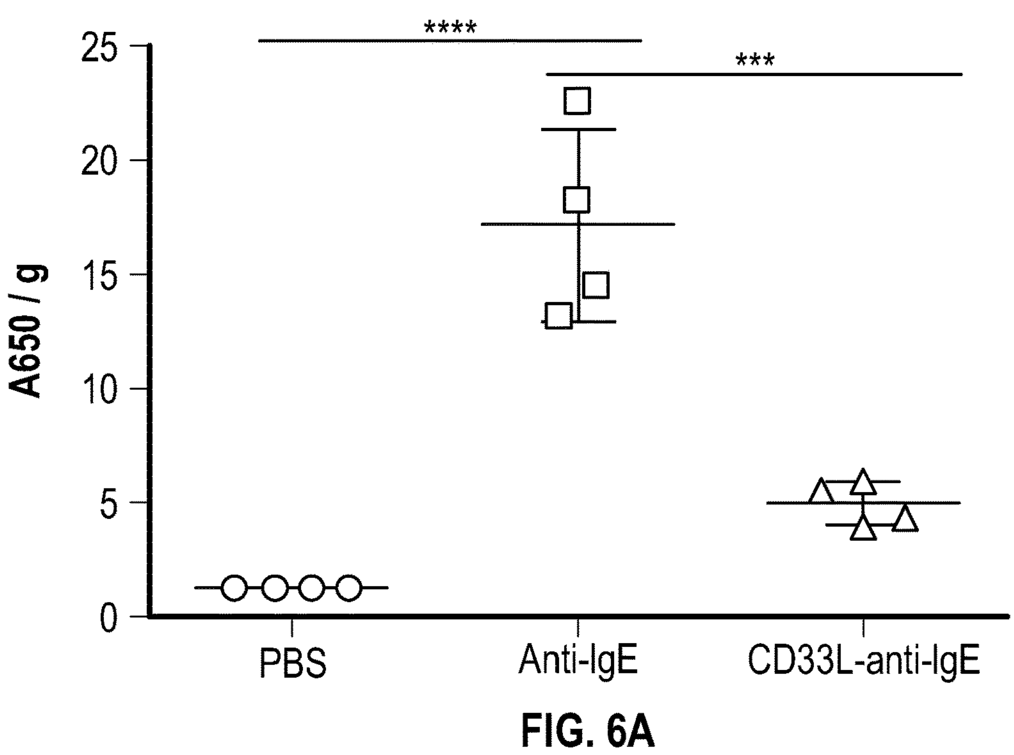
FIG. 6A-6B illustrate the impact of CD33L-anti-IgE conjugates on induction of passive cutaneous anaphylaxis in mouse ears.

FIG. 6A shows that CD33L conjugated to anti-IgE suppressed passive cutaneous anaphylaxis in mice that express the human CD33 Siglec (i.e., in hFcεRI$^+$ CD33$^+$ (hFcεR1+ mFcεR1− MCPT5Cre+ hCD33+/+ mice).

Figure 6B:
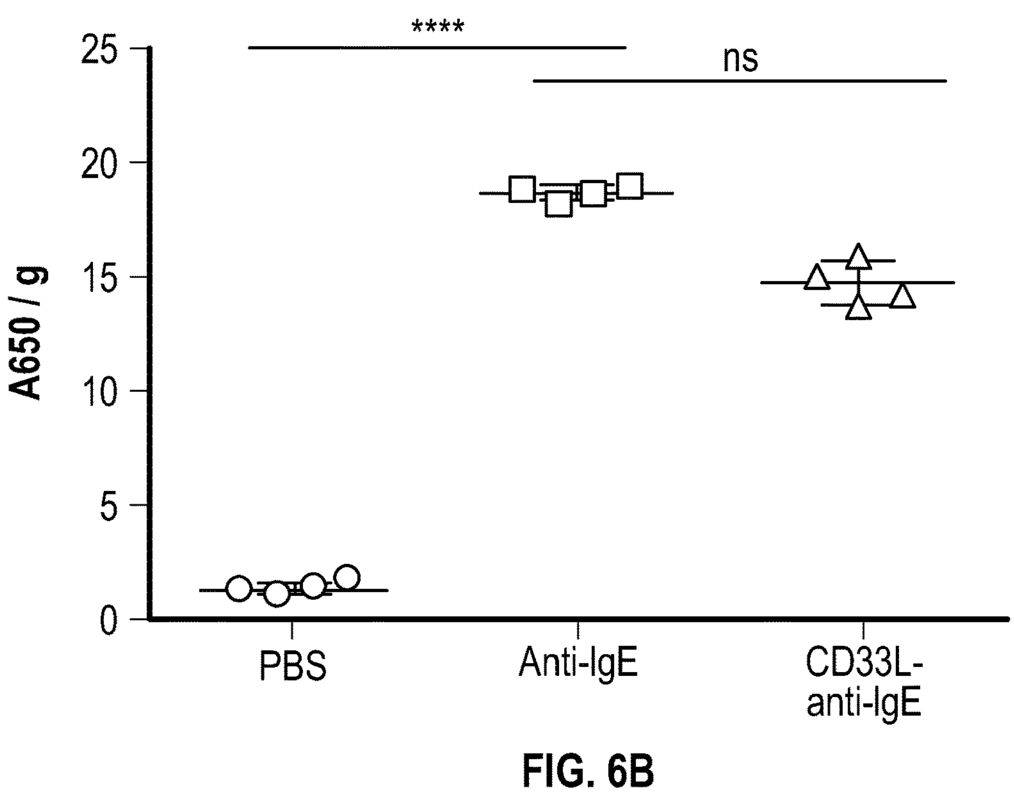

However, no such suppression of anaphylaxis was observed in similarly treated mice that did not express the human CD33 Siglec (FIG. 6B). Both anti-IgE and CD33L-anti-IgE triggered passive cutaneous anaphylaxis in mice that did not express the human CD33 Sigler (hFcεR1+ mFcεR1− MCPT5Cre−hCD33$^{-/-}$) mice.

Example 7: Treatment with CD33L-Anti-IgE Conjugates Reduces Anaphylactic Responses in Mice This Example shows that treating mice with CD33L-anti-IgE conjugates reduces anaphylaxis in mice.

Mice were pre-sensitized to anti-OVA-human IgE (1 μg/mice). One day later, the mice were treated with human anti-IgE conjugated to CD33L (5 μg/mice) or with non-conjugated human anti-IgE (control), and then challenged with human anti-IgE antibody (2 μg/mice). The rectal temperature of mice was monitored at 10-minute intervals as a measure of anaphylactic response.

Figure 7A:
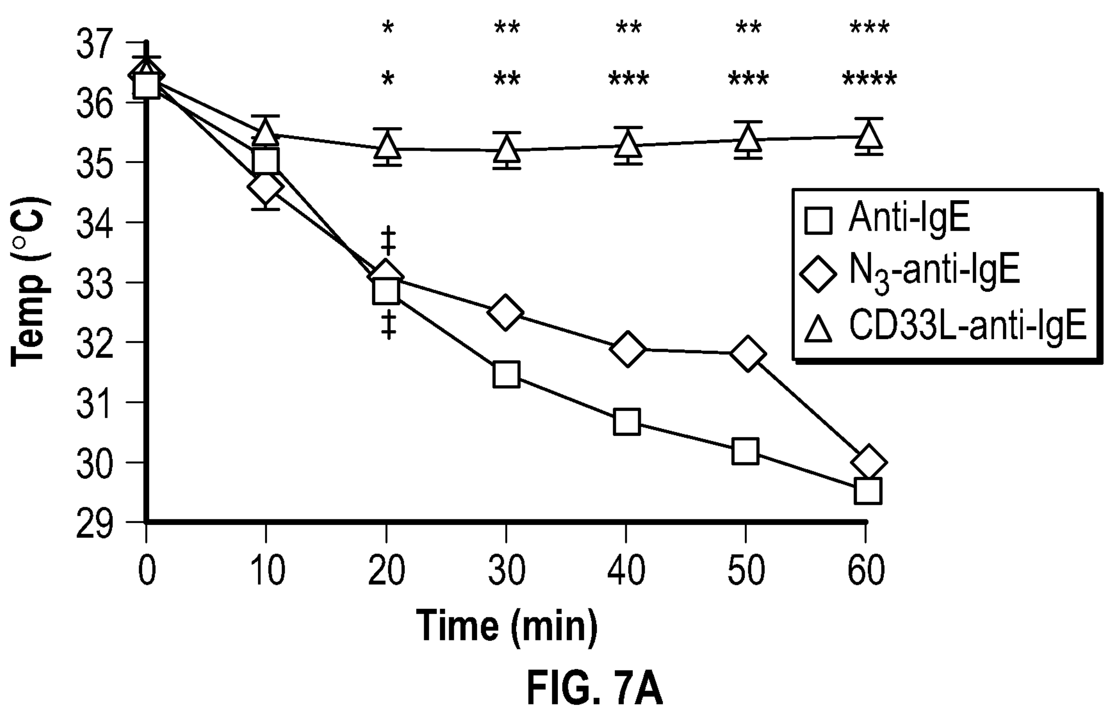
FIGS. 7A-7C illustrate the impact of CD33-L-anti-IgE conjugates on the induction of passive systemic anaphylaxis and desensitization to antigen challenges. Anaphylaxis reduces the temperature of the mice and was used as a measure of the extent of anaphylaxis.
Figure 7B:
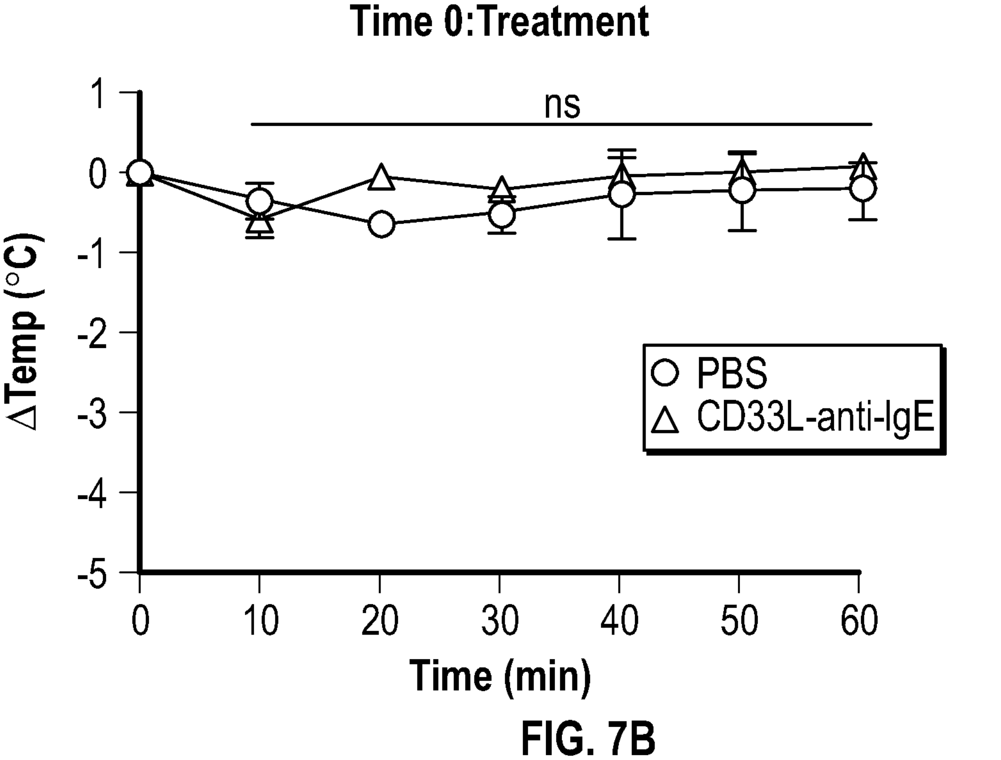

As shown in FIGS. 7A and 7B, the CD33L-anti-IgE conjugate suppressed passive systematic anaphylaxis in NSG-SGM3-CD34+ humanized mice. The results in FIG. 7A were analyzed by Two-way ANOVA followed by Tukey's test (*P<0.05,P<0.01,*P<0.001 **P<0.0001) Results in FIG. 7B-7C were analyzed by Two-way ANOVA followed by Sidak's multiple test (*P=0.0002 and ****P<0.0001). The change in temperature (ΔT) reflects the changes in rectal temperature.

Figure 7C:
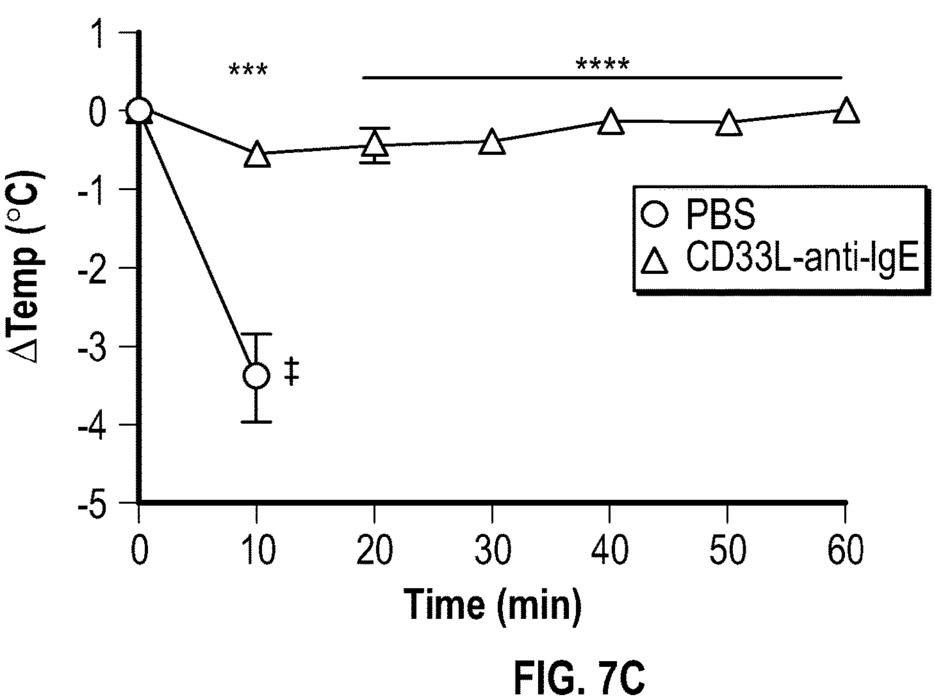

FIG. 7C shows that CD33L-anti-IgE conjugates protect mice from systematic anaphylaxis upon subsequent challenge with anti-IgE.

Example 8: Ligands for Various Siglecs

Various glycan ligands were evaluated for binding to Siglec-2, Siglec-3, Siglec-8 and Siglec-10.

Five replicates of each glycan were printed at 100 μM or 3 μM printing concentration in 150 mM phosphate buffer, 0.005% Tween-20, pH 8.2, using technique described by Rillahan et al. Angew. Chem., Int. Ed. Engl., 2012, 51, 11014-11018 (2012)); Blixt et al. J. Am. Chem. Soc., 2008, 130, 6680-6681 (2008); Blixt et al. Proc. Natl. Acad. Sci. U.S.A. 101: 17033-17038 (2004)). Siglec-Fc chimeras were produced in-house using stable expression in CHO cells (hCD33 and mSn) or transient transfection into COS-cells as described by Blixt et al. (J. Biol. Chem., 2003, 278, 31007-31019 (2003)). The human Siglec-Fc was applied to the array at various concentrations, the arrays were washed by dipping three times into a reservoir of PBS-Tween, followed by detection with the labelled secondary antibody (10 mg ml-1). Final washes in both procedures included dipping three times into reservoirs of PBS-Tween, PBS, and $H_2O$, followed by centrifugation to dry. Slides were then scanned on a Perkin-Elmer ProScanArray Express and the images processed using IMAGENE.

Table 3 illustrates which ligands bind to Siglec-2, Siglec-3, Siglec-8 and Siglec-10.

TABLE 3

Ligand Specificity for Different Siglecs

| Siglec ligand | Siglecs | | | |
|---|---|---|---|---|
| | Siglec 2 | Siglec3 | Siglec 8 | Siglec 10 |
| 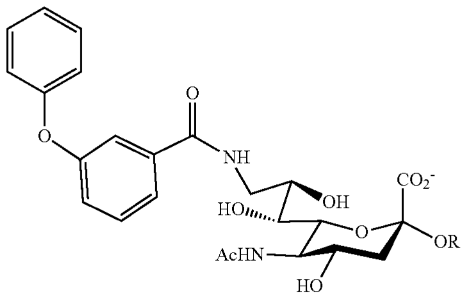 | + | − | ND | ND |
| 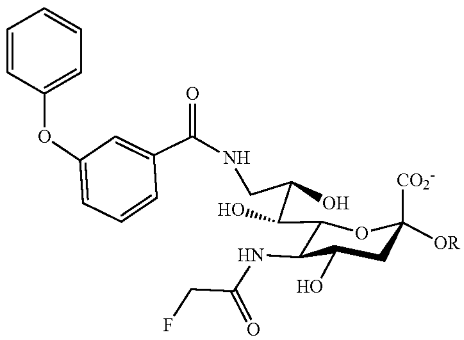 | + | − | ND | ND |
| 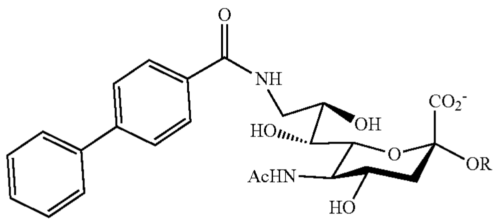 | + | − | ND | ND |

TABLE 3-continued
| Ligand Specificity for Different Siglecs | | | | |
|---|---|---|---|---|
| | Siglecs | | | |
| Siglec ligand | Siglec 2 | Siglec3 | Siglec 8 | Siglec 10 |
| 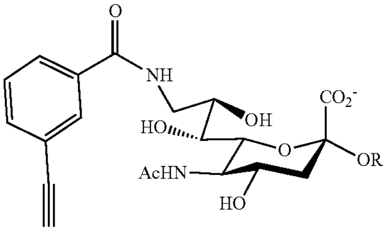 | + | + | ND | ND |
| 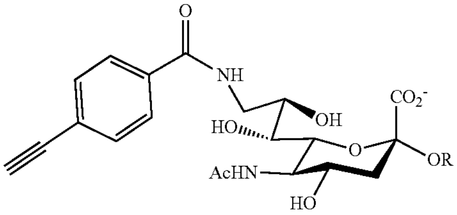 | + | − | ND | ND |
| 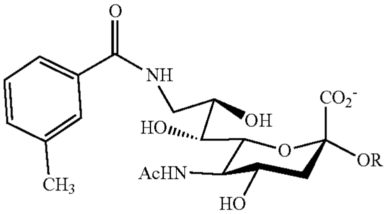 | + | + | ND | ND |
| 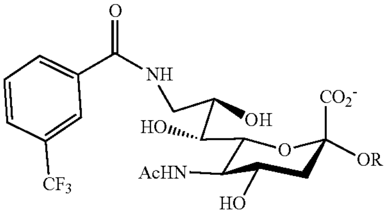 | + | − | ND | ND |
| 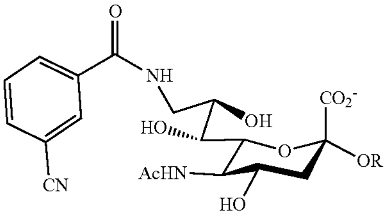 | + | − | ND | ND |
| 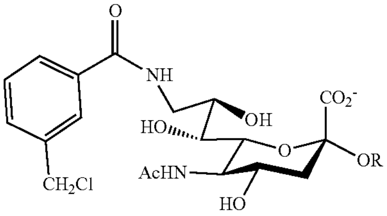 | + | − | ND | ND |

TABLE 3-continued
| Ligand Specificity for Different Siglecs | | | | |
|---|---|---|---|---|
| | Siglecs | | | |
| Siglec ligand | Siglec 2 | Siglec3 | Siglec 8 | Siglec 10 |
| 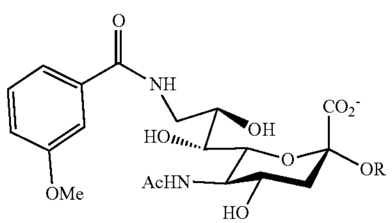 | + | − | ND | ND |
| 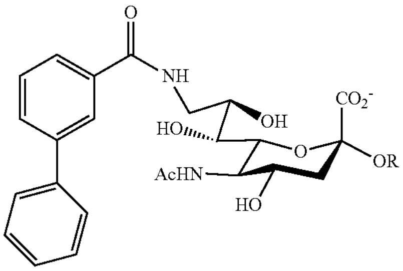 | + | − | ND | ND |
| 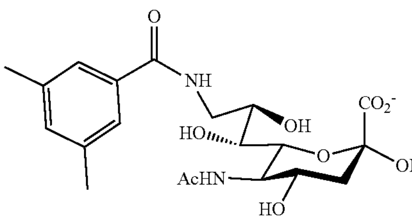 | + | + | ND | ND |
| 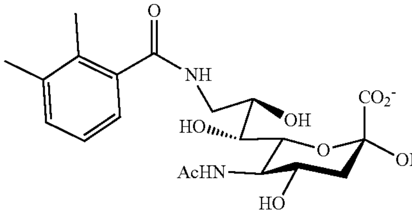 | + | − | ND | ND |
| 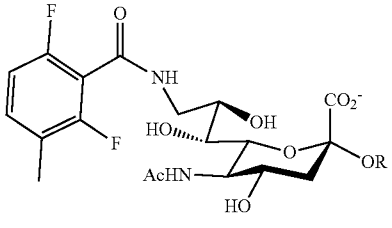 | + | − | ND | ND |
| 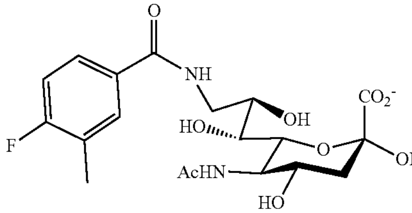 | + | + | ND | ND |

TABLE 3-continued
| Ligand Specificity for Different Siglecs | | | | |
|---|---|---|---|---|
| | Siglecs | | | |
| Siglec ligand | Siglec 2 | Siglec3 | Siglec 8 | Siglec 10 |
| 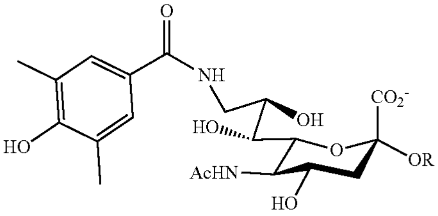 | + | + | ND | ND |
| 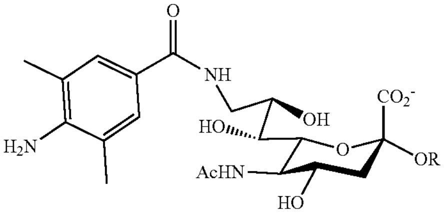 | + | + | ND | ND |
| 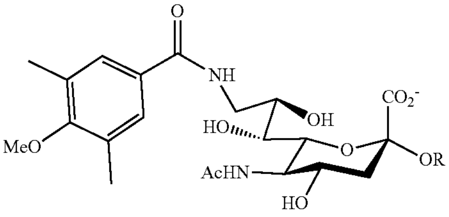 | − | + | ND | ND |
| 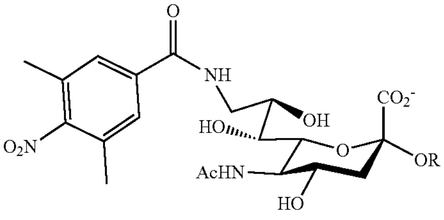 | − | + | ND | ND |
| 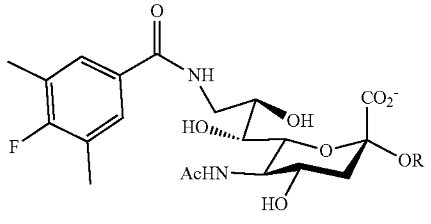 | − | + | ND | ND |

TABLE 3-continued
Ligand Specificity for Different Siglecs
| Siglec ligand | Siglecs | | | |
|---|---|---|---|---|
| | Siglec 2 | Siglec3 | Siglec 8 | Siglec 10 |
| 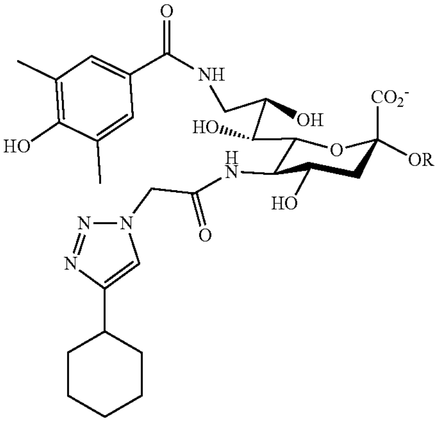 | – | + | ND | ND |
| 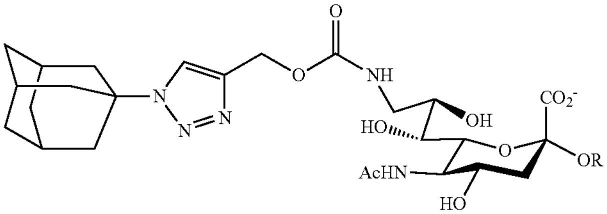 | ND | ND | ND | + |
| 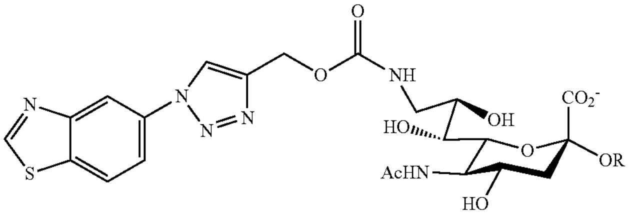 | ND | ND | ND | + |
| 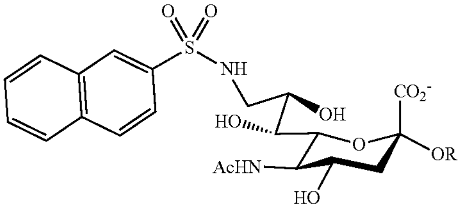 | – | + | + | ND |
| 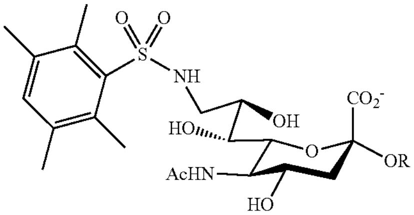 | ND | ND | + | ND |

TABLE 3-continued
| Ligand Specificity for Different Siglecs | | | | |
|---|---|---|---|---|
| | Siglecs | | | |
| Siglec ligand | Siglec 2 | Siglec3 | Siglec 8 | Siglec 10 |
| 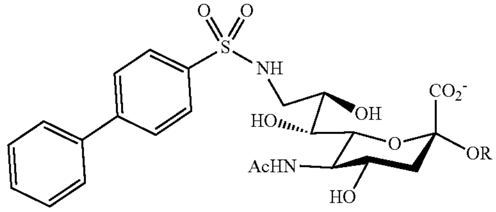 | ND | ND | + | ND |
| 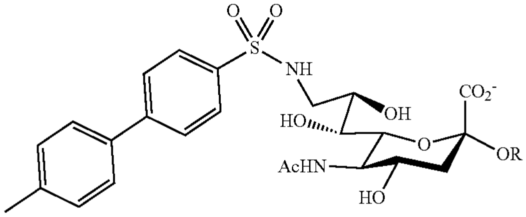 | ND | ND | + | ND |
| 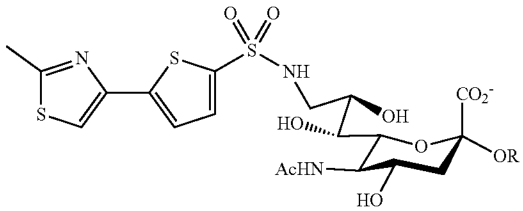 | ND | ND | + | ND |
| 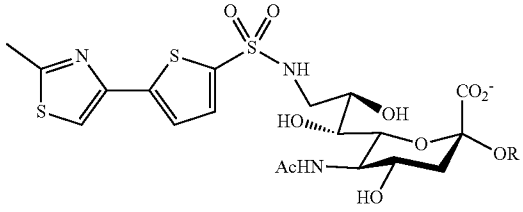 | ND | ND | + | ND |
| 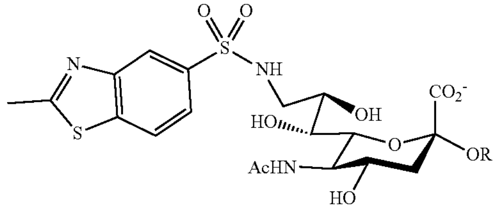 | ND | ND | + | ND |
| 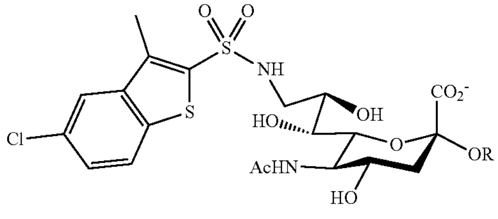 | ND | ND | + | ND |

TABLE 3-continued

| Ligand Specificity for Different Siglecs | | | | |
|---|---|---|---|---|
| | Siglecs | | | |
| Siglec ligand | Siglec 2 | Siglec3 | Siglec 8 | Siglec 10 |
| 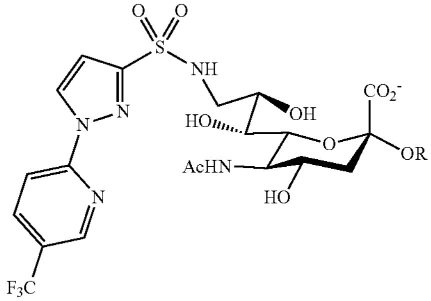 | ND | ND | + | ND |

R = Glycan backbone;
ND = Not Determine.

Example 9: Conjugation of Synthetic High Affinity Siglec3 Ligands (CD33L) to Antibodies This Example illustrates methods for conjugating polymeric Siglec3 ligands (CD33L) to antibodies, including the anti-IgE antibodies used in Example 10.

A schematic diagram for chemical conjugation of high affinity CD33L to a polymer is shown below. In general, polylysine was used as a polymer for displaying about 10-15 Siglec ligands and then the polylysine-Siglec ligand complexes were linked to anti-IgE antibodies.

Each of the polylysine polymers (PLLs) employed had just one azido functional group and about 70 units of lysine. Among 70 units of lysines, only 10-15 units were modified with maleimide-peg6-NHS (by amide bond formation), which generated a polymer with about 10-15 units of maleimide functionalized peg6 linkers. Since maleimide functional group is reactive to thiol (—SH) functional group, a Siglec ligand with a sulfhydryl group (CD33LSH) was used to react with the maleimide functionalized polymer, thereby generating CD33 ligand functionalized polymers. In the last step, CD33 ligand functionalized polymers were conjugated to anti-IgE antibodies that had a strained cyclic alkyne (BCN) functional group by using copper free azide-alkyne click chemistry. This synthetic method is illustrated by the following diagram.

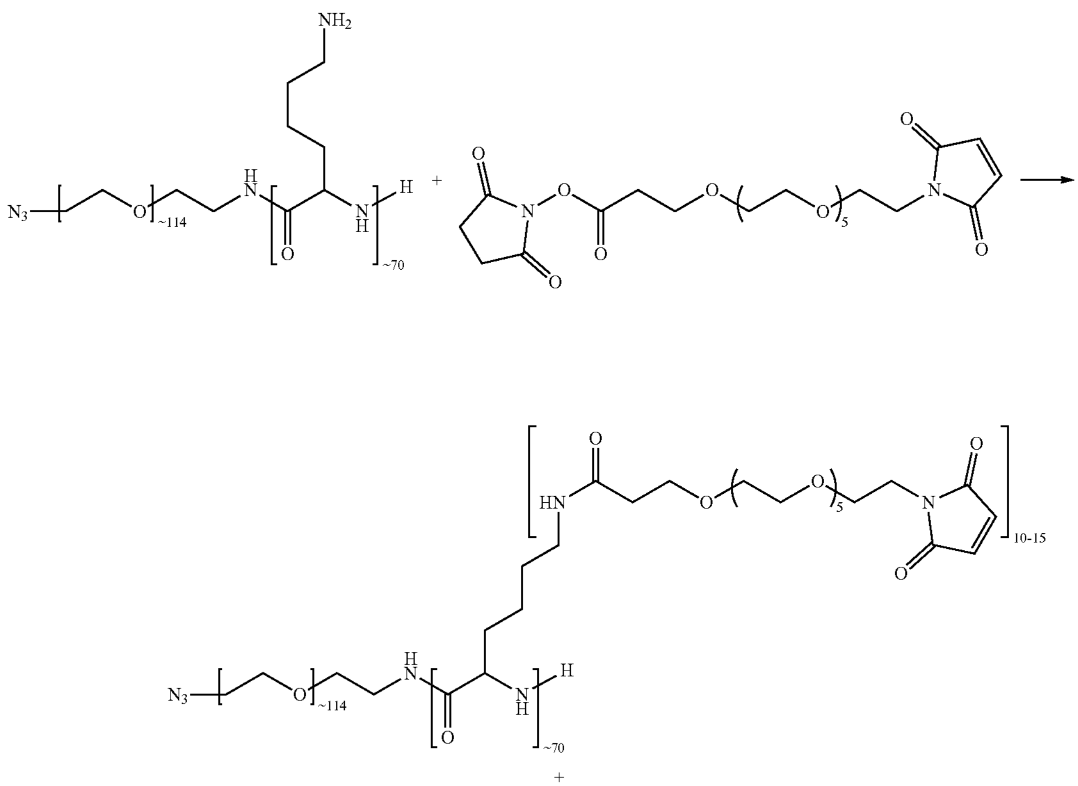

-continued

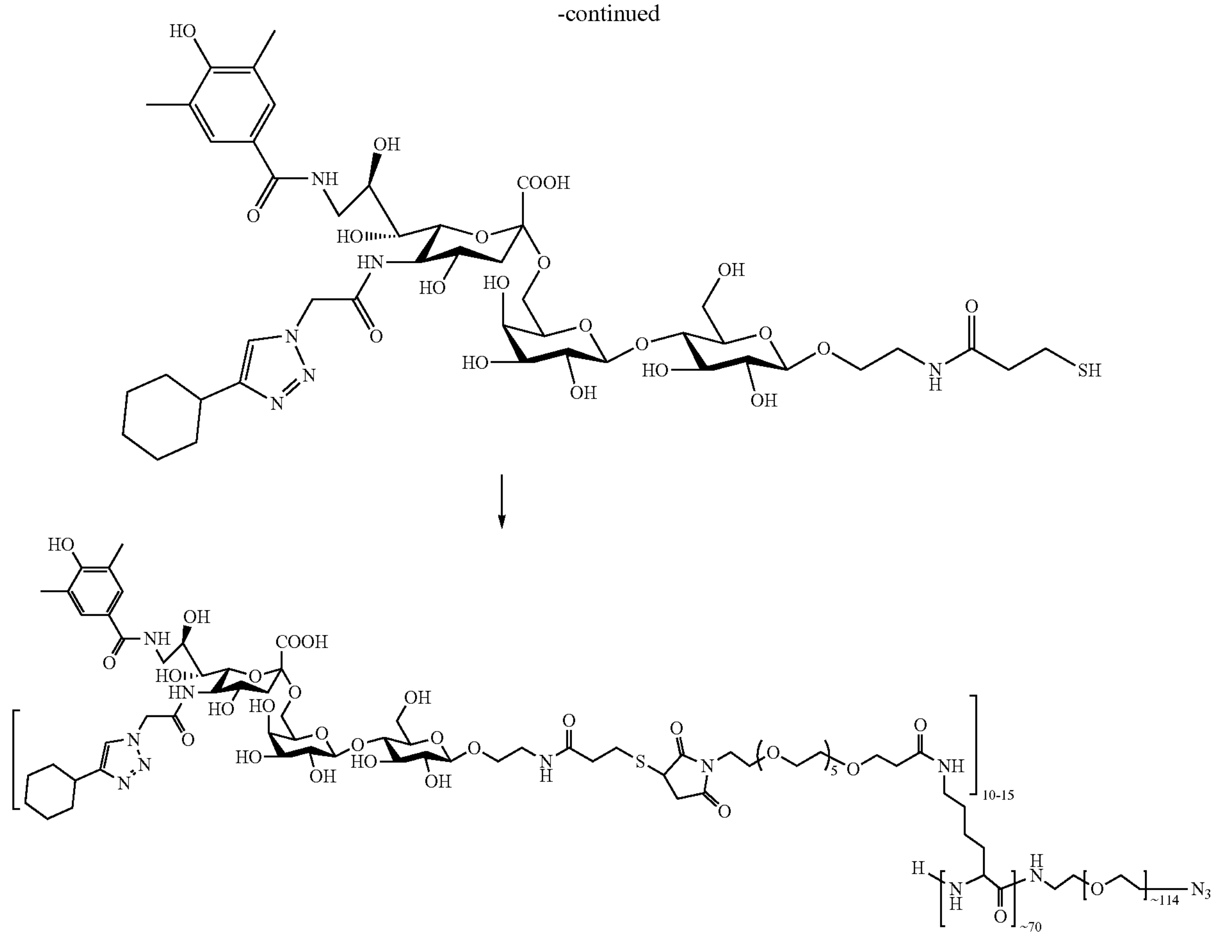

In the first step shown above, about 10-15 units of lysine residues of polylysine (e.g., with about 70 lysine residues) were reacted with maleimide-amido-peg6-NHS groups of a selected spacer. The CD33 ligand having a sulfhydryl (SH) functional group was then reacted via thiol-maleimide conjugation with a multifunctional polymer that had a series of monomers, each displaying maleimide.

The CD33 ligand-polymer linked to azido functional group was then reacted with an antibody that is functionalized with at least three strained alkyne BCN groups as shown below (the large Y represents an antibody).

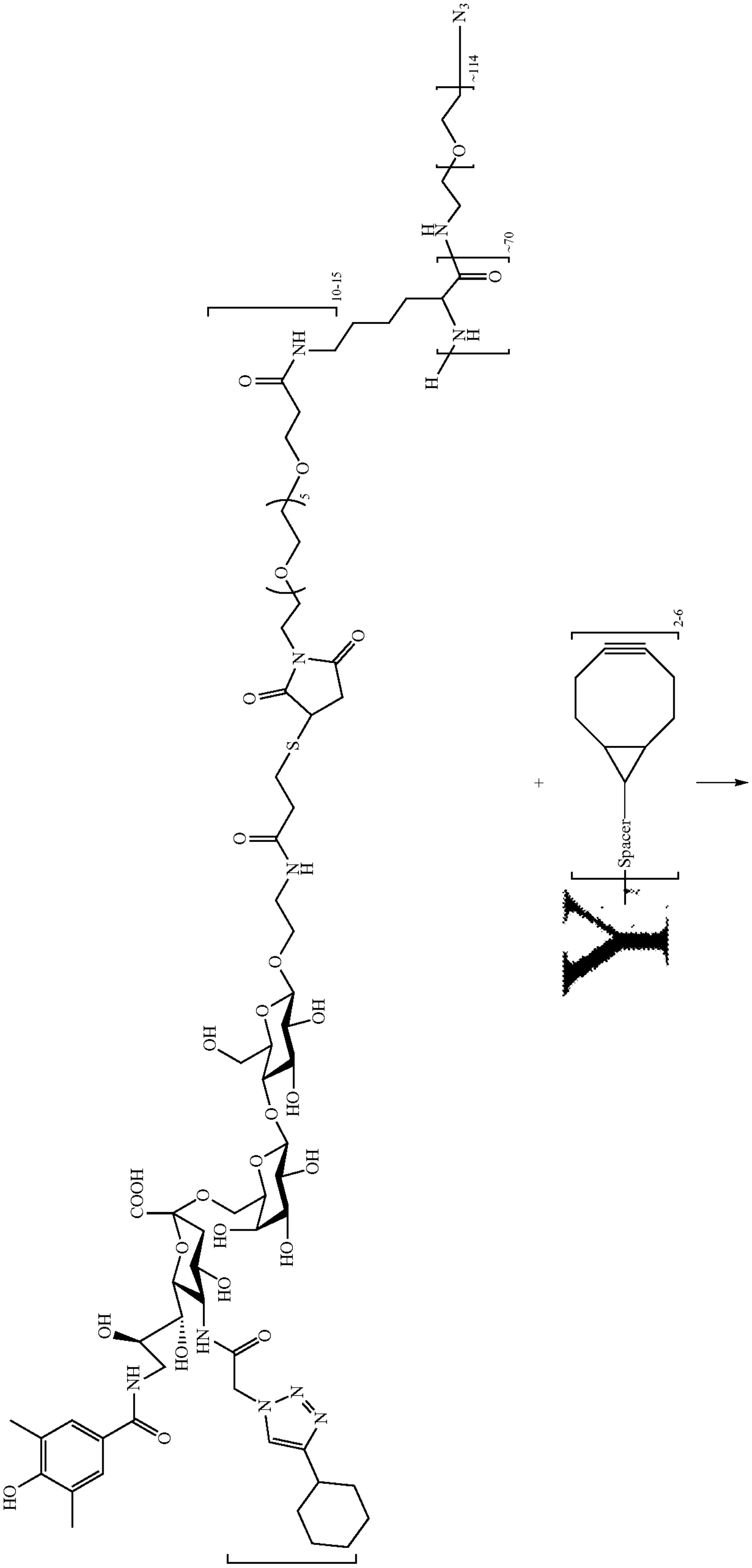

-continued
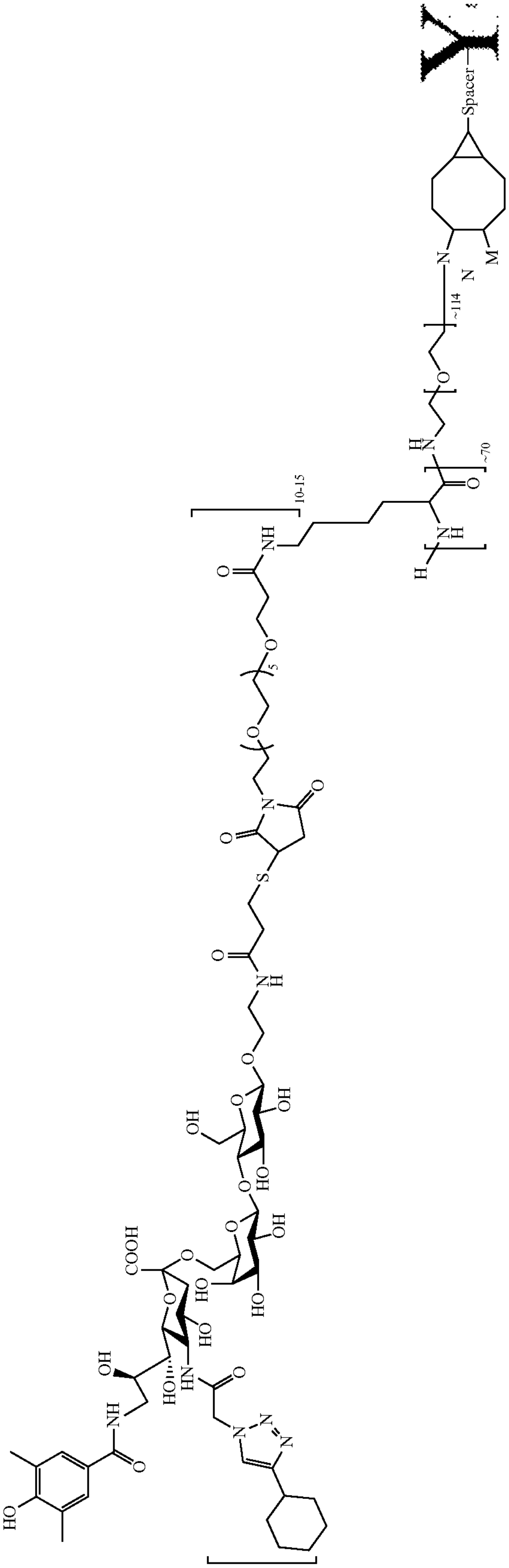

Example 10: CD33 Ligand-Anti-IgE Antibody Conjugates Suppress Anaphylaxis

This Example illustrates that conjugation of CD33-L to anti-IgE antibodies as described in Example 9 results in suppression of anti-IgE mediated passive systemic anaphylaxis (PSA) and desensitizes mast cells to subsequent to antigen challenge.

Experiments were performed using human CD34+ stem cell NSG-SGM3 mice that are populated with human mast cells ('humanized mice'). The impact of the CD33L conjugated to anti-IgE on induction of PSA was assessed after the mice were sensitized with anti-OVA-human IgE (400 ng/mice). One day later the mice were treated with human anti-IgE with or without conjugated CD33L (2.5 μg/mice). Anaphylaxis was assessed by a drop in rectal temperature with measurements at 10 min intervals.

As illustrated in FIGS. 8A-8E, anti-IgE-CD33L suppresses anaphylaxis and desensitizes mice to subsequent antigen challenge. Mice were pre-sensitized with one clone of anti-OVA-human IgE (11B6) and 2 different clones of anti-Arah2-hIgE (2C9 and 16A8). (400 ng/mouse). One day later mice were treated twice (time zero, FIG. 8B and time 5 h, FIG. 8C) with anti-human IgE with/without CD33L (2.5 μg/mice) and the assessed for anaphylaxis by monitoring the temperatures of the animals, where a drop in temperature indicates that anaphylaxis is occurring. As shown in FIG. 8A-8E little or no anaphylaxis was observed.

Figure 8A:
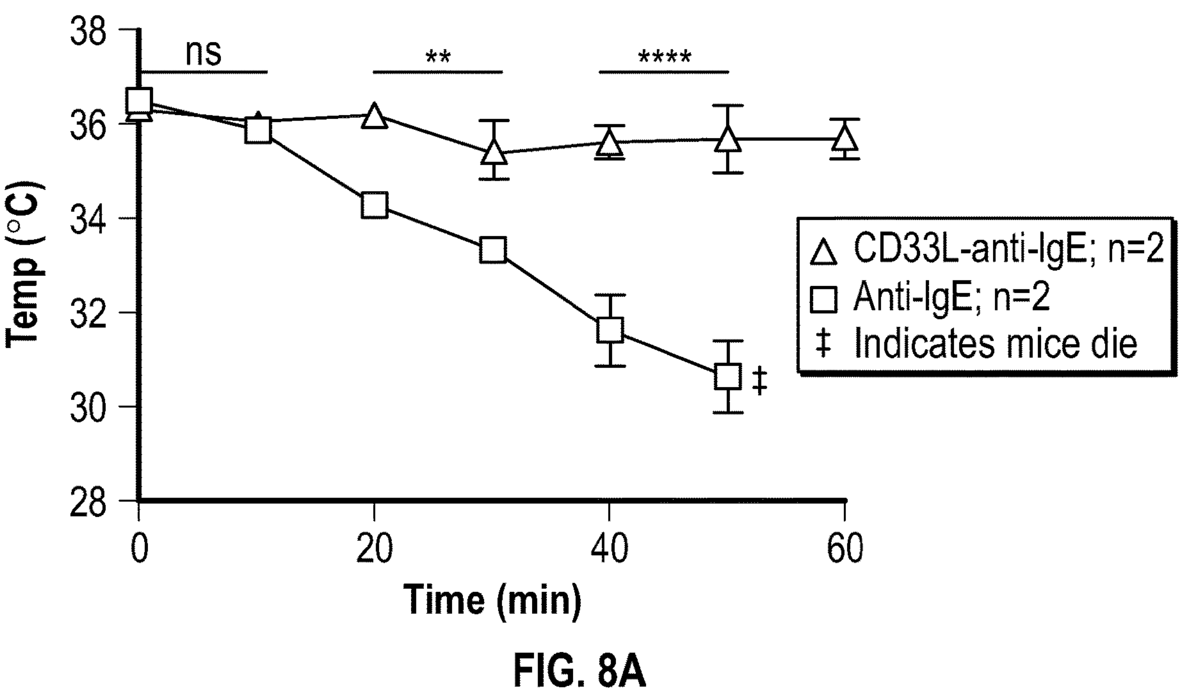
FIG. 8A-8E show that conjugation of CD33-L to anti-IgE as illustrated in Example 9 results in suppression of anti-IgE mediated passive systemic anaphylaxis (PSA) and desensitizes mast cells to subsequent to antigen challenge.
Figure 8B:
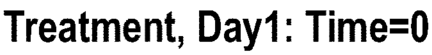
Figure 8B:
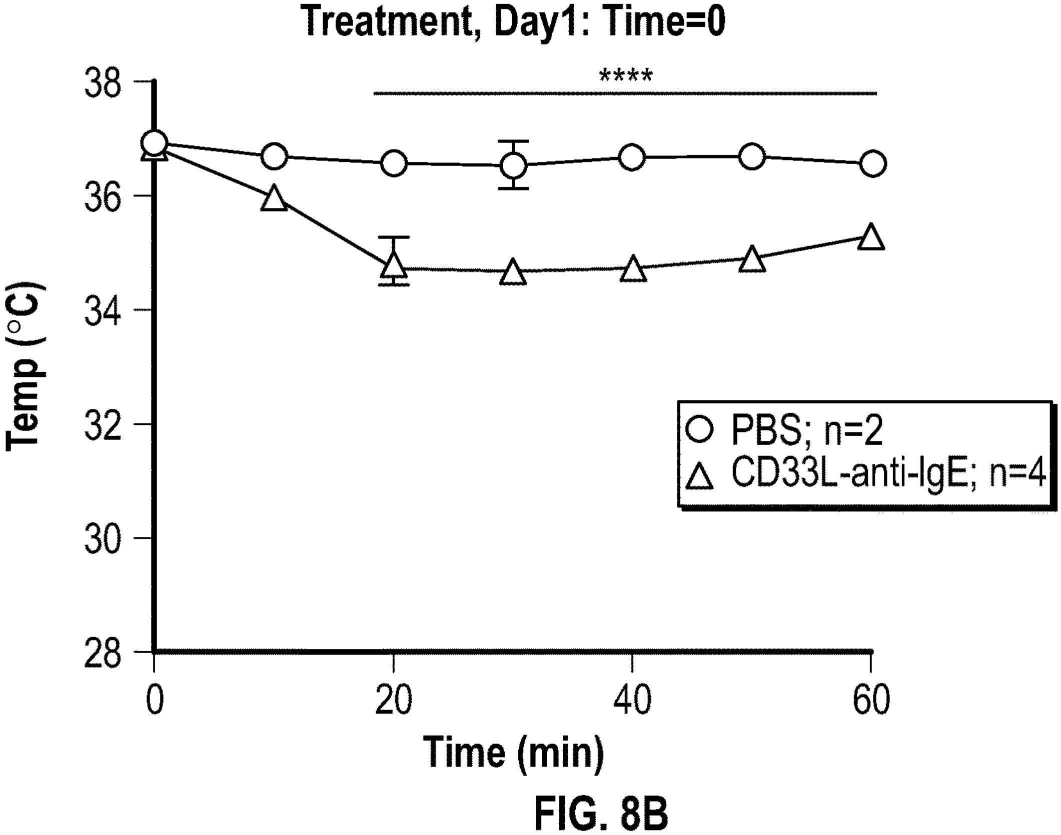
Figure 8C:
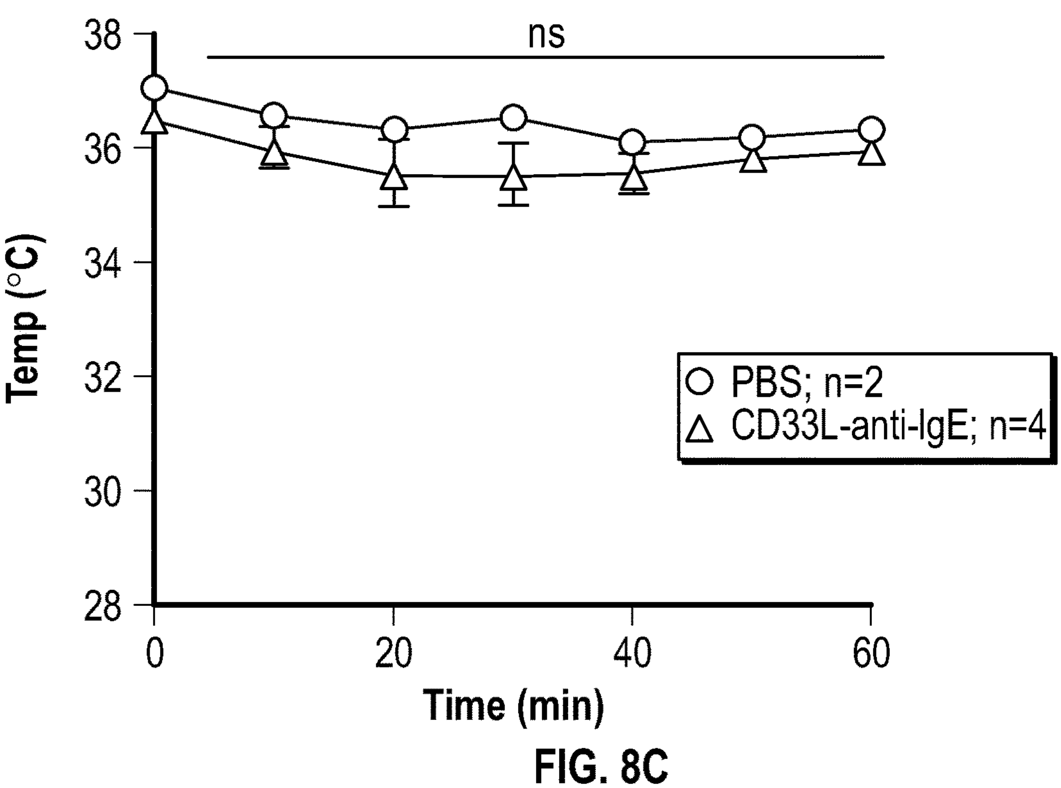
Figure 8D:
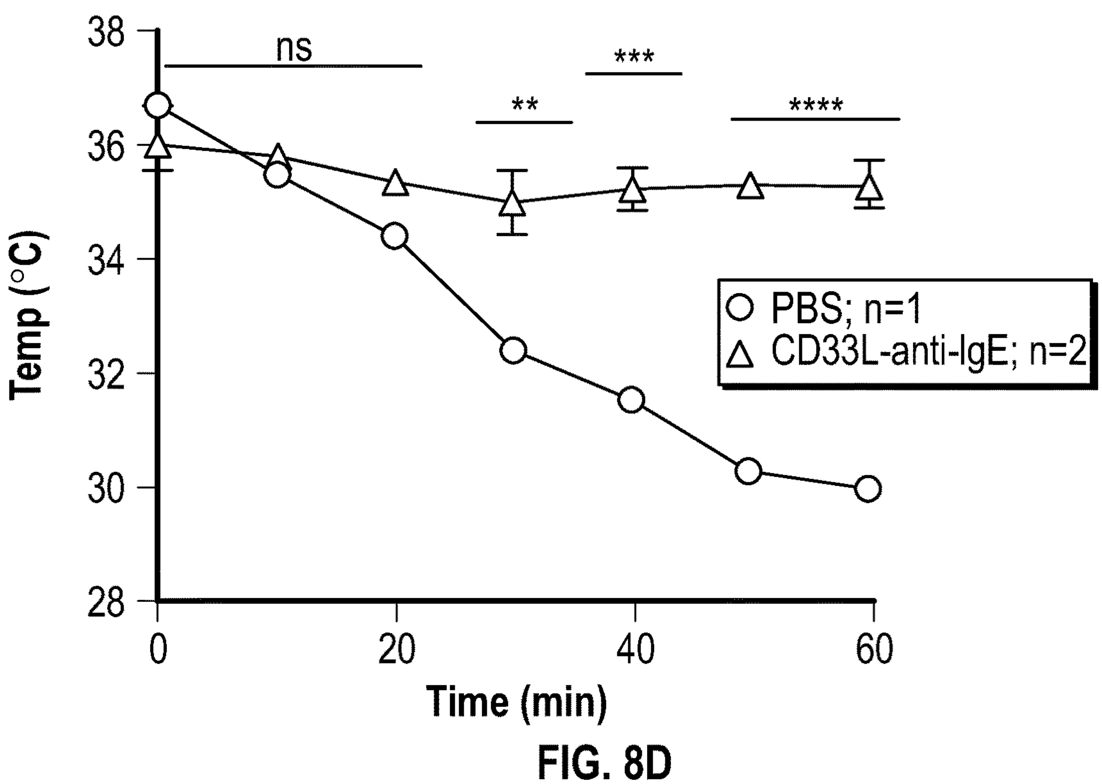
Figure 8E:
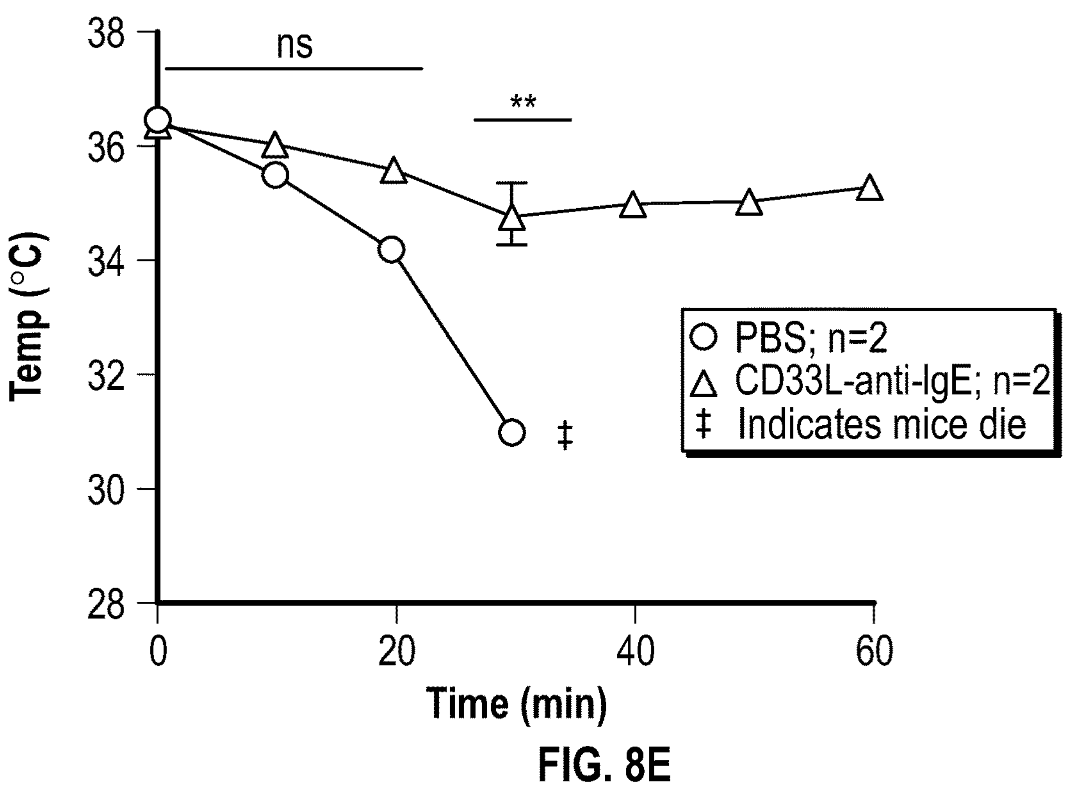

After another 24 hours mice were challenged with antigen. The antigens were OVA-liposomes (OVA-LP; 0.2 ml of 1 mM lipid, 0.05% OVA-lipid in phosphate buffered saline) administered intravenously (FIG. 8D) or peanut extract (10 μg in 0.2 ml phosphate buffered saline) intraperitoneally (FIG. 8E). After challenge the change in rectal temperature of mice was measured at 10-minute intervals. FIGS. 8D-8E show that treatment of anti-IgE-CD33L protects mice from anaphylaxis, and that the mice are subsequently desensitized to subsequence challenge.

REFERENCES

1. Bednar, K. J. et al. Exploiting CD22 To Selectively Tolerize Autoantibody Producing B-Cells in Rheumatoid Arthritis. *ACS Chem Biol* 14, 644-654 (2019).
2. Bednar, K. J. et al. Human CD22 Inhibits Murine B Cell Receptor Activation in a Human CD22 Transgenic Mouse Model. *J Immunol* 199, 3116-3128 (2017).
3. Pang, L., Macauley, M. S., Arlian, B. M., Nycholat, C. M. & Paulson, J. C. Encapsulating an Immunosuppressant Enhances Tolerance Induction by Siglec-Engaging Tolerogenic Liposomes. *Chembiochem* 18, 1226-1233 (2017).
4. Orgel, K. A. et al. Exploiting CD22 on antigen-specific B cells to prevent allergy to the major peanut allergen Ara h 2. *J Allergy Clin Immunol* 139, 366-369 e362 (2017).
5. Pfrengle, F., Macauley, M. S., Kawasaki, N. & Paulson, J. C. Copresentation of antigen and ligands of Siglec-G induces B cell tolerance independent of CD22. *J Immunol* 191, 1724-1731 (2013).
6. Macauley, M. S. et al. Antigenic liposomes displaying CD22 ligands induce antigen-specific B cell apoptosis. *J Clin Invest* 123, 3074-3083 (2013).
7. Duan, S. et al. CD33 recruitment inhibits IgE-mediated anaphylaxis and desensitizes mast cells to allergen. *J Clin Invest* 129, 1387-1401 (2019).
8. Galli, S. J. Recruiting CD33 on mast cells to inhibit IgE-mediated mast cell-dependent anaphylaxis. *J Clin Invest* 129, 955-957 (2019).
9. Kawasaki, N., Rademacher, C. & Paulson, J. C. CD22 regulates adaptive and innate immune responses of B cells. *J Innate Immun* 3, 411-419 (2011).

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements are intended to describe and summarize various embodiments of the invention according to the foregoing description in the specification.

STATEMENTS

1. A conjugate between at least two Siglec ligands and an anti-receptor antibody, where the Siglec ligands and the anti-receptor antibody are covalently linked.

2. The conjugate of statement 1, wherein each Siglec ligand can bind to a Siglec-2 (CD22).

3. The conjugate of statement 1, wherein each Siglec ligand can bind to a Siglec-3 (CD33).

4. The conjugate of statement 1, wherein each Siglec ligand can bind to a Siglec-8.

5. The conjugate of statement 1-3 or 4, wherein the antibody is conjugated to more than one, more than two, or more than three, or more than four, or more than five, or more than six, or more than seven, or more than eight, or more than nine, or more than ten, or more than eleven, or more than twelve, or more than thirteen, or more than fourteen, or more than fifteen of the same Siglec ligands.

6. The conjugate of statement 1-4 or 5, wherein each Siglec ligand is conjugated to the anti-receptor antibody at a site that is not in the antigen binding site of the anti-receptor antibody.

7. The conjugate of statement 1-5 or 6, wherein the anti-receptor antibody binds to a cellular receptor of an immune cell.

8. The conjugate of statement 1-5 or 6, wherein the anti-receptor antibody binds to a cellular receptor complex of an immune cell.

9. The conjugate of statement 1-7 or 8, wherein the anti-receptor antibody binds to an antibody already bound to a cellular receptor.

10. The conjugate of statement 7, 8 or 9, wherein the cellular receptor or the cellular receptor complex is an IgD B cell receptor or an IgM B cell receptor.

11. The conjugate of statement 10, wherein the anti-receptor antibody binds to the IgD or IgM component or the B cell receptor complex.

12. The conjugate of statement 7, 8 or 9, wherein the cellular receptor is an Fc cellular receptor.

13. The conjugate of statement 12, wherein the cellular receptor complex is an FcεRI cellular receptor.

14. The conjugate of statement 12 or 13, wherein the cellular receptor complex is an IgE/FcεRI complex.

15. The conjugate of statement 7-13 or 14, wherein the anti-receptor antibody can bind via its antigen binding site to the cellular receptor or the cellular receptor complex.

16. The conjugate of statement 7-14 or 15, wherein the cellular receptor or the cellular receptor complex is on a B cell or a mast cell.

17. The conjugate of statement 1-15 or 16, where the conjugate inhibits allergic responses to an allergen.

18. The conjugate of statement 17, wherein the allergen is a hapten such as 2,4,6-trinitrophenol; an antibiotic such as a β-lactam antibiotic (including penicillins and cephalosporin), a monobactam (e.g., aztreonam), a carbapenem (e.g., imipenem, meropenem), a clavam (e.g., clavulanic acid), a carbacephem (e.g., loracarbef), a sulfonamide (e.g., sulfamethoxazole, sulfamerazine, sulfamethazine), an antibacterial trimethoprim; a neuromuscular blocking drug such as promethazine, neostigmine, or morphine; a food allergen such as egg (ovalbumin), cow (e.g., Bos d 11, Bos d 4, Bos d5, Bos d 6, Bos d 8, etc.), peanut (e.g., Ara h 2, Ara h 1, Ara h 3, Ara h 6, etc.), hazelnut (e.g., Cor a 9, Car a 11, Cor a 14, etc.), walnut, casein, soy (e.g., GLy m 5, Gly m 6, etc.), malt, or shellfish; an environmental allergen such as mouse (e.g., Mus m 1), rat (e.g., Rat n 1), cat (e.g., Fel d 1), dog (e.g., Can f 1), bee, wasp, house dust mite (e.g., Der p 1), short ragweed pollen (e.g., Amb a 1), Birch pollen (e.g. Bet v 1), *Aspergillus* (e.g., Asp r 1), cockroach (e.g., Bla g 2), a tree (e.g., pine pollen, Latex, rubber, *Hevea brasiliensis*); a therapeutic agent (e.g., factor VIII, interferon, erythropoietin); an antibody (e.g., anti-human IgE, anti-human IgE receptor, human IgE, infliximab, adalimumab, trastuzumab, bevacizumab, rituximab, cetuximab, and fragments thereof), and combinations thereof.

19. The conjugate of statement 1-17, or 18, wherein each Siglec ligand is conjugated directly to the anti-receptor antibody.

20. The conjugate of statement 1-17, or 18, wherein each Siglec ligand is conjugated indirectly to the anti-receptor antibody.

21. The conjugate of statement 20, wherein each Siglec ligand is conjugated indirectly to the antibody via a linker.

22. The conjugate of statement 1-20, wherein the Siglec ligand is a compound of Formula I.

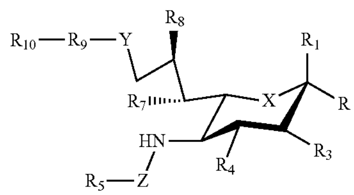

where:

X can be a methylene ($CH_2$) or a heteroatom (e.g., O, N, or S);

R can be a linker, an antibody, or $R_2$-R6;

$R_1$ can be hydrogen, carboxylate, aldehyde (CHO), phosphate or sulfate;

$R_2$ can be a bond, a heteroatom, an alkene, an alkyne, an alkoxy, an alkyl, an alkyl-heterocycloalkyl-alkyl, a hydroxy, a heterocycle, or an oligosaccharide;

$R_3$, $R_4$, $R_7$ and $R_8$ can each independently be hydrogen, azido, amino, or hydroxyl;

$R_5$ can be a hydrogen, alkyl, alkene, alkyne, aryl, alkylaryl, heteroaryl, or alkylheteroaryl, wherein the alkyl, alkene, aryl, alkylaryl, heteroaryl, or alkylheteroaryl group(s) can be substituted with one or more substituents selected from hydroxy, amino, azido, cyano, nitro, halo, alkyl, $CF_3$, alkoxy, carboxylate, ether, cycloalkyl, lower alkenyl, lower alkynyl, phenyl, benzyl, phenoxy, heteroaryl, alkylheteroaryl, heteroarylalkyl, amidoheteroaryl, alkoxyamidoheteroaryl, or alkylhalide group;

$R_6$ can be an antibody;

Y can be a heteroatom, amino, carbamate, carboxyl, carboxylate, methylene, amide, —$CH_2$-carbamate, —$CH_2$-sulfonamide, sulfonyl, —$CH_2$-sulfonyl, sulfonamide, urea, $CH_2$-urea, thiourea, or —$CH_2$-thiourea;

Z can be a carbonyl, carboxylate, methylene, acyl, aryl, heteroaryl, sulfonyl, —$CH_2$-sulfonyl, sulfonamide, —$CH_2$-sulfonamide, urea, —$CH_2$-urea, thiourea, —$CH_{12}$-thiourea;

$R_9$ can be a hydrogen, hydroxyl, alkyl, alkoxy, aryl, arylalkyl, arylalkoxy, alkoxyaryl, heteroaryl, alkylheteroaryl, or heterocycle, where the $R_9$ alkyl, alkoxy, alkylamino, aryl, arylalkyl, arylalkoxy, alkoxyaryl, heteroaryl, alkylheteroaryl, or heterocycle group(s) can be substituted with one or more substituents selected from hydrogen, hydroxy, alkyl, alkyne, alkoxy, amino, azido, cyano, nitro, halo, haloalkyl, $CF_3$, carboxylate, ether, or cycloalkyl groups; and, $R_{10}$ can be a hydrogen, alkyl, aryl, oxyaryl, heteroaryl, cycloalkyl, or bicycloalkyl, where the $R_{10}$ alkyl, aryl, oxyaryl, heteroaryl, cycloalkyl, or bicycloalkyl group(s) can be substituted with one or more substituents selected from hydrogen, alkyl, halo, $CF_3$, alkoxy, amino, azido, cyano, or nitro.

23. The conjugate of statement 1-21 or 22, wherein the Siglec ligand is a compound of Formula II:

II

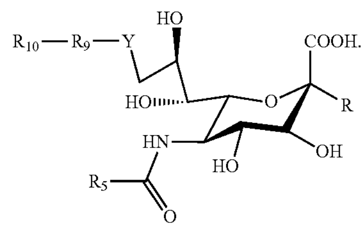

wherein:

R can be a linker, an antibody, or $R_2$-R6;

$R_2$ can be a bond, a heteroatom, an alkene, an alkyne, an alkoxy, an alkyl, an alkyl-heterocycloalkyl-alkyl, a hydroxy, a heterocycle, or an oligosaccharide;

$R_6$ can be an antibody;

Y can be a heteroatom, amino, carbamate, carboxyl, carboxylate, methylene, amide, —$CH_2$-carbamate, —$CH_2$-sulfonamide, —$CH_2$-amide, sulfonyl, —$CH_2$-sulfonyl, sulfonamide, urea, $CH_2$-urea, thiourea, or —$CH_2$-thiourea;

$R_5$ can be a hydrogen, alkyl, alkene, alkyne, aryl, alkylaryl, heteroaryl, or alkylheteroaryl, wherein the alkyl, alkene, aryl, alkylaryl, heteroaryl, or alkylheteroaryl group(s) can be substituted with one or more substituents selected from hydroxy, amino, azido, cyano, nitro, halo, alkyl, $CF_3$, alkoxy, carboxylate, ether, cycloalkyl, lower alkenyl, lower alkynyl, phenyl, benzyl, phenoxy, heteroaryl, alkylheteroaryl, heteroarylalkyl, amidoheteroaryl, alkoxyamidoheteroaryl, or alkylhalide group;

$R_9$ can be a hydrogen, hydroxyl, alkyl, alkoxy, aryl, arylalkyl, arylalkoxy, alkoxyaryl, heteroaryl, alkylheteroaryl, or heterocycle, where the $R_9$ alkyl, alkoxy, alkylamino, aryl, arylalkyl, arylalkoxy, alkoxyaryl, heteroaryl, alkylheteroaryl, or heterocycle group(s) can be substituted with one or more substituents selected from hydrogen, hydroxy, alkyl, alkyne, alkoxy, amino, azido, cyano, nitro, halo, haloalkyl, $CF_3$, carboxylate, ether, or cycloalkyl groups; and, $R_{10}$ can be a hydrogen, alkyl, aryl, oxyaryl, heteroaryl, cycloalkyl, or bicycloalkyl, where the $R_{10}$ alkyl, aryl, oxyaryl, heteroaryl, cycloalkyl, or bicycloalkyl group(s) can be substituted with one or more substituents selected from hydrogen, alkyl, halo, $CF_3$, alkoxy, amino, azido, cyano, or nitro.

24. The conjugate of statement 22 or 23, wherein the $R_5$ alkyl, alkene, aryl, alkylaryl, heteroaryl, or alkylheteroaryl can have 1 to 2, or 1 to 3, or 1 to 4 substituents selected from one or more substituents selected from hydroxy, amino, azido, cyano, nitro, halo, alkyl, $CF_3$, alkoxy, carboxylate, ether, cycloalkyl, lower alkenyl, lower alkynyl, phenyl, benzyl, phenoxy, heteroaryl, alkylheteroaryl, heteroarylalkyl, amidoheteroaryl, alkoxyamidoheteroaryl, or alkylhalide groups. In some cases, the R5 alkyl, alkene, aryl, alkylaryl, heteroaryl, or alkylheteroaryl groups can have 1, 2, 3, 4, or 5 substituents selected from halo, alkyl, $CF_3$, alkoxy, carboxylate, ether, cycloalkyl, lower alkenyl, lower alkynyl, phenyl, benzyl, phenoxy, heteroaryl, alkylheteroaryl, heteroarylalkyl, amidoheteroaryl, alkoxyamidoheteroaryl, or alkylhalide groups.

25. The conjugate of statement 22, 23 or 24, wherein the R9 alkyl, alkoxy, aryl, arylalkyl, arylalkoxy, alkoxyaryl, heteroaryl, alkylheteroaryl, or heterocycle group(s) can have 1 to 2, or 1 to 3, or 1 to 4 substituents selected from hydrogen, hydroxy, alkyl, alkyne, alkoxy, amino, azido, cyano, nitro, halo, haloalkyl, $CF_3$, carboxylate, ether, or cycloalkyl groups. In some cases, the R9 alkyl, alkoxy, aryl, arylalkyl, arylalkoxy, alkoxyaryl, heteroaryl, alkylheteroaryl, or heterocycle group(s) can have 1, 2, 3, 4, or 5 substituents selected from hydrogen, hydroxy, alkyl, alkyne, alkoxy, amino, azido, cyano, nitro, halo, haloalkyl, $CF_3$, carboxylate, ether, or cycloalkyl groups.

26. The conjugate of statement 22-24 or 25, wherein the $R_{10}$ alkyl, aryl, oxyaryl, heteroaryl, cycloalkyl, and/or bicycloalkyl group(s) can have 1 to 2, or 1 to 3, or 1 to 4 substituents selected from hydrogen, alkyl, halo, $CF_3$, alkoxy, amino, azido, cyano, or nitro groups. In some cases, $R_{10}$ alkyl, aryl, oxyaryl, heteroaryl, cycloalkyl, and/or bicycloalkyl group(s) can have 1, 2, 3, 4, or 5 substituents selected from hydrogen, alkyl, halo, $CF_3$, alkoxy, amino, azido, cyano, or nitro groups.

27. The conjugate of statement 1-25 or 26, comprising at least one unnatural R, $R_5$ or $R_9$ substituent.

28. The conjugate of statement 1-26 or 27, wherein the Siglec ligand is one of the following compounds:

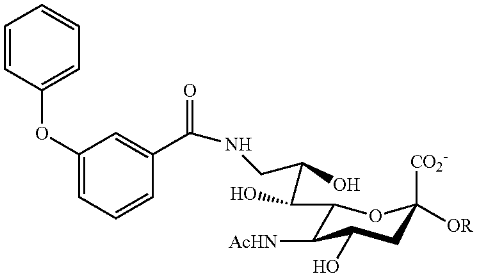

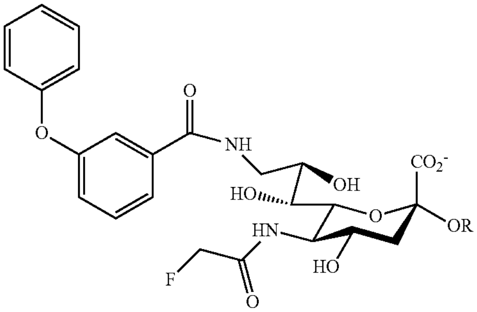

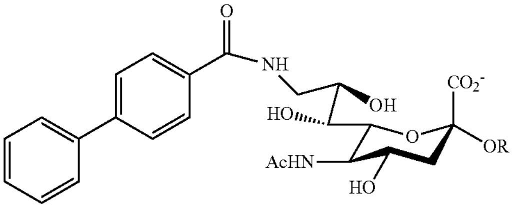

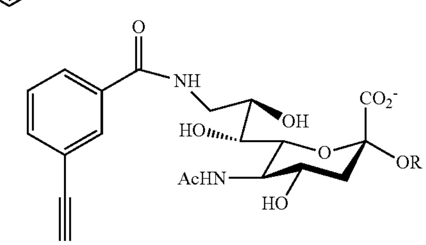

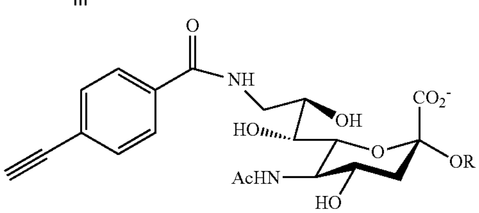

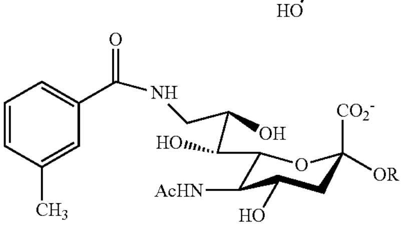

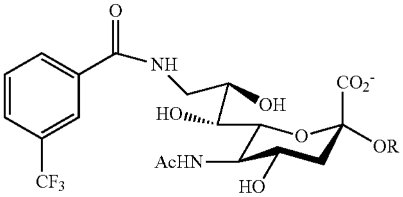

-continued
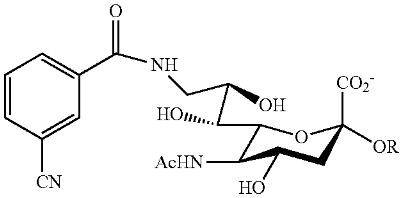
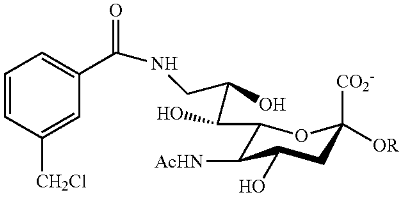
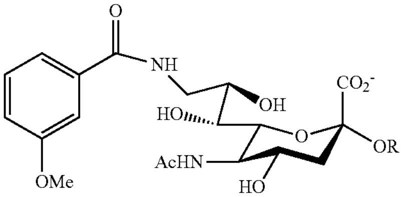
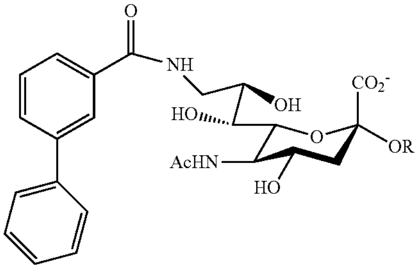
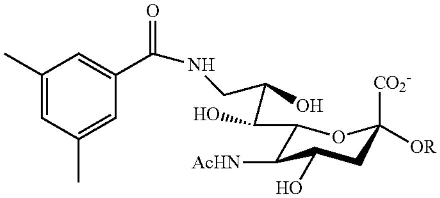
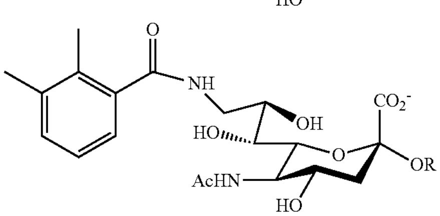
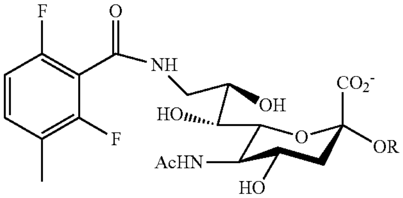
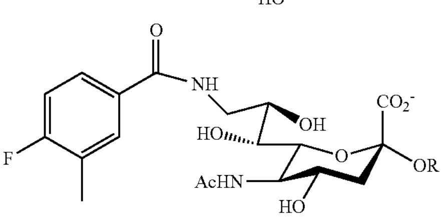
-continued
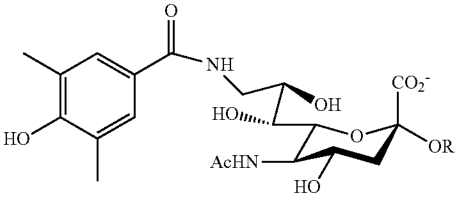
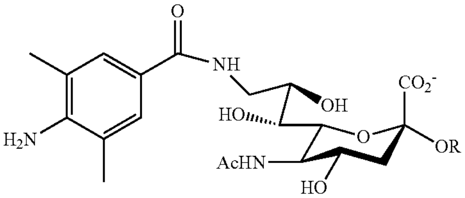
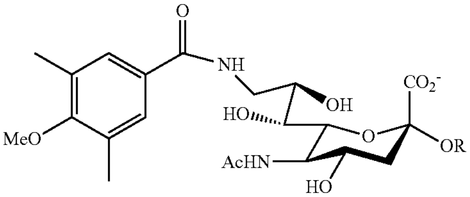
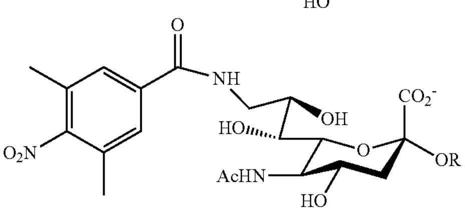
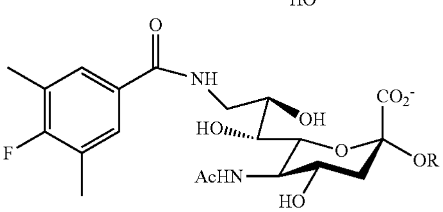
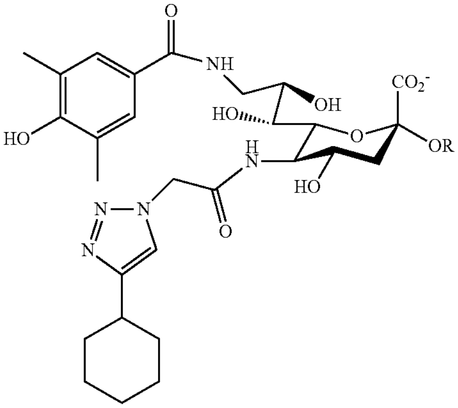
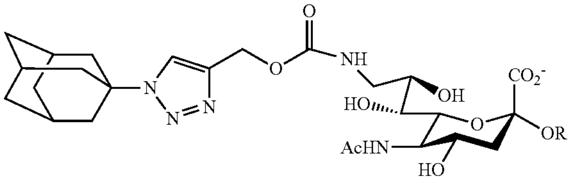

-continued

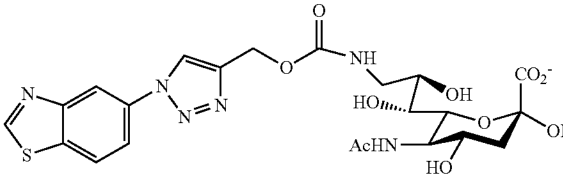

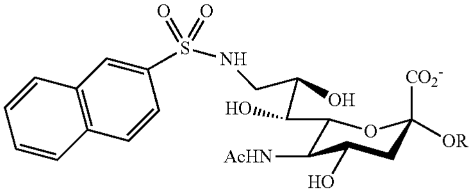

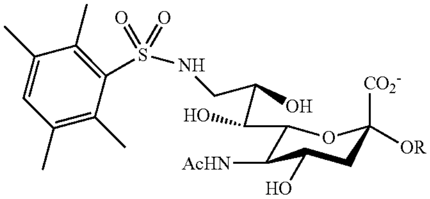

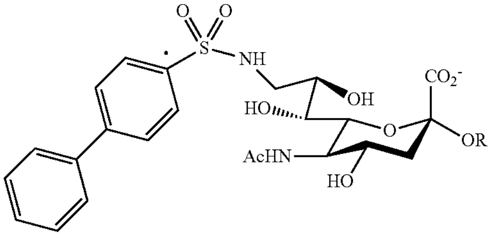

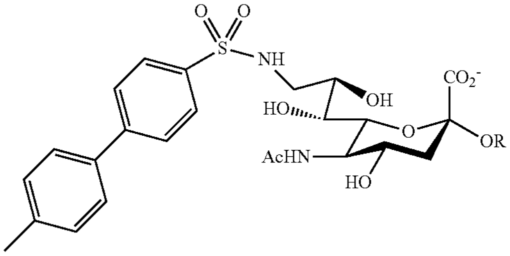

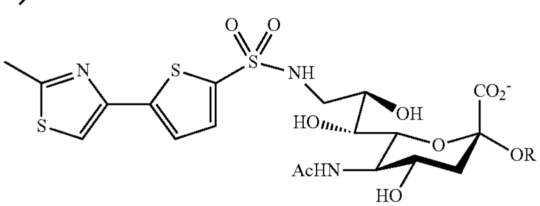

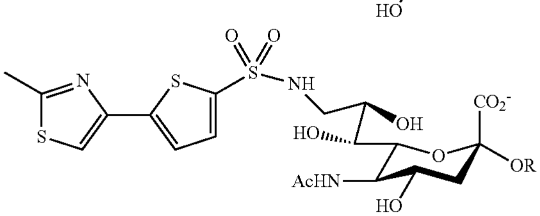

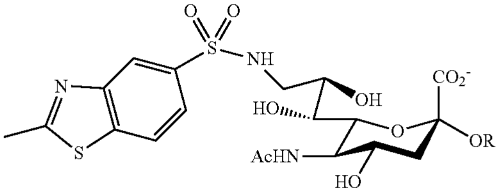

-continued

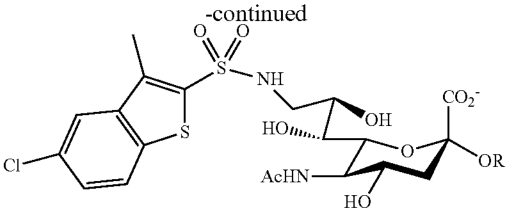

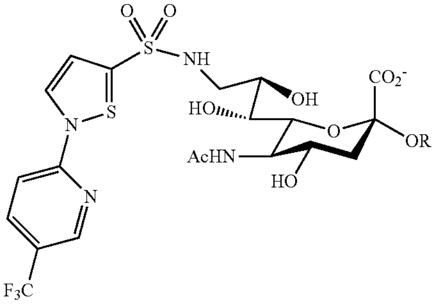

29. A method comprising administering to a subject a composition comprising the conjugate of statement 1-27 or 28.

30. The method of statement 29, wherein the subject has, or is suspected of having or developing, an allergic response, an immune disease or an immune condition.

31. The method of statement 30, wherein the immune disease or immune condition is an allergy, allergic rhinitis, allergic asthma, non-allergic asthma, atopic dermatitis, allergic gastroenteropathy, anaphylaxis, urticaria, food allergies, allergic bronchopulmonary aspergillosis, parasitic diseases, interstitial cystitis, hyper-IgE syndrome, ataxia-telangiectasia, Wiskott-Aldrich syndrome, athymic lymphoplasia, IgE myeloma, graft-versus-host reaction, allergic purpura, rheumatoid arthritis, ulcerative colitis, crones disease, immune thrombocytopenia (ITP), thrombotic thrombocytopenic purpura (TTP), or a combination thereof.

32. The method of statement 29, 30 or 31, wherein the subject has, or is suspected of having or developing, an immune response to any of the following antigens: 2,4,6-trinitrophenol; an antibiotic such as a β-lactam antibiotic (including penicillins and cephalosporin), a monobactam (e.g., aztreonam), a carbapenem (e.g., imipenem, meropenem), a clavam (e.g., clavulanic acid), a carbacephem (e.g., loracarbef), a sulfonamide (e.g., sulfamethoxazole, sulfamerazine, sulfamethazine), an antibacterial trimethoprim; a neuromuscular blocking drug such as promethazine, neostigmine, or morphine; a food allergen such as egg (ovalbumin), cow (e.g., Bos d 11, Bos d 4, Bos d5, Bos d 6, Bos d 8, etc.), peanut (e.g., Ara h 2, Ara h 1, Ara h 3, Ara h 6, etc.), hazelnut (e.g., Cor a 9, Car a 11, Cor a 14, etc.), walnut, casein, soy (e.g., GLy m 5, Gly m 6, etc.), malt, or shellfish; an environmental allergen such as mouse (e.g., Mus m 1), rat (e.g., Rat n 1), cat (e.g., Fel d 1), dog (e.g., Can f 1), bee, wasp, house dust mite (e.g., Der p 1), short ragweed pollen (e.g., Amb a 1), Birch pollen (e.g. Bet v 1), *Aspergillus* (e.g., Asp r 1), cockroach (e.g., Bla g 2), a tree (e.g., pine pollen, Latex, rubber, *Hevea brasiliensis*); a therapeutic agent (e.g., factor VIII, interferon, erythropoietin); an antibody (e.g., anti-human IgE, anti-human IgE receptor, human IgE, infliximab, adalimumab, trastuzumab, bevacizumab, rituximab, cetuximab, and fragments thereof), and combinations thereof.

33. The method of statement 29-31 or 32, wherein the subject is a human, a domesticated animal, a zoo animal, or an experimental animal.

34. The method of statement 29-32 or 33, which reduces mast cell degranulation after administration to the subject, compared to levels of mast cell degranulation before administration to the subject with an immune disease or immune condition.

35. The method of statement 29-33 or 34, which reduces mast cell degranulation by at least 25%.

36. The method of statement 29-34 or 35, which reduces mast cell degranulation by at least 25% upon subsequent exposure of the subject to the antigen.

37. The method of statement 29-35 or 36, which reduces anaphylaxis after administration to the subject, compared to levels of anaphylaxis before administration to the subject with an immune disease or immune condition.

38. The method of statement 29-36 or 37, which reduces anaphylaxis in the subject by at least 50%.

39. The method of statement 29-37 or 38, which reduces anaphylaxis in the subject by at least 50% upon subsequent exposure of the subject to the antigen.

40. The method of statement 29-38 or 39, further comprising administering an antigen selected from an antibiotic, an antibacterial agent, a neuromuscular blocking drug, a food allergen, a therapeutic agent, an antibody, or a combination thereof to the subject.

The specific methods, devices and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention.

The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

What is claimed:

1. A conjugate comprising at least 10 to 15 sialic acid-binding immunoglobulin-type lectins (Siglecs) ligands, each linked to an anti-receptor antibody, wherein the Siglec ligands bind to Siglec-2, Siglec-3, or Siglec-8, and wherein the anti-receptor antibody binds to a B cell receptor, a B cell receptor complex, a receptor for a Fc region of immunoglobulin E (FcεRI), or a FcεRI complex.

2. The conjugate of claim 1, wherein the conjugate suppresses activation of a B cell receptor.

3. The conjugate of claim 1, wherein the conjugate suppresses activation of the FcεRI receptor complexed with an IgE antibody.

* * * * *